United States Patent
Nakatsugawa et al.

(10) Patent No.: US 12,254,608 B2
(45) Date of Patent: Mar. 18, 2025

(54) SAMPLE ACQUISITION INFORMATION MANAGEMENT DEVICE, SAMPLE ACQUISITION INFORMATION MANAGEMENT SYSTEM, AND SAMPLE ACQUISITION INFORMATION MANAGEMENT METHOD

(71) Applicant: FUJIFILM Corporation, Tokyo (JP)

(72) Inventors: Haruyasu Nakatsugawa, Ashigarakami-gun (JP); Seiji Yamashita, Ashigarakami-gun (JP); Tatsuya Ishizaka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1157 days.

(21) Appl. No.: 17/033,087

(22) Filed: Sep. 25, 2020

(65) Prior Publication Data

US 2021/0010998 A1 Jan. 14, 2021

Related U.S. Application Data

(63) Continuation of application No. PCT/JP2019/012374, filed on Mar. 25, 2019.

(30) Foreign Application Priority Data

Mar. 28, 2018 (JP) .................. 2018-062721

(51) Int. Cl.
*G06T 7/00* (2017.01)
*A61B 5/15* (2006.01)
(Continued)

(52) U.S. Cl.
CPC .......... *G06T 7/0002* (2013.01); *A61B 5/1405* (2013.01); *A61J 1/05* (2013.01); *G02B 26/10* (2013.01)

(58) Field of Classification Search
CPC ........ G06T 7/0002; A61B 5/1405; A61J 1/05; G16H 10/40; G16H 30/20; G09B 23/00; G09B 23/28

See application file for complete search history.

(56) References Cited

U.S. PATENT DOCUMENTS

2013/0331664 A1* 12/2013 Gilad-Gilor ........... A61B 5/741
600/407
2014/0073880 A1* 3/2014 Boucher ................ G16H 30/20
600/109
(Continued)

FOREIGN PATENT DOCUMENTS

CN 1871995 A 12/2006
CN 101226664 A 7/2008
(Continued)

OTHER PUBLICATIONS

Regan, Caitlin Anderson. "Laser Speckle Imaging of Blood Flow Beneath Static Scattering Media." Order No. 10286674 University of California, Irvine, 2017. Ann Arbor: ProQuest. Web. Dec. 4, 2024. (Year: 2017).*

(Continued)

*Primary Examiner* — Lena Najarian
(74) *Attorney, Agent, or Firm* — Birch, Stewart, Kolasch & Birch, LLP

(57) ABSTRACT

There are provided a sample acquisition information management device, a sample acquisition information management system, and a sample acquisition information management method that allow a subject who is to collect a sample by oneself to reliably perform a sample acquisition operation. Each of the sample acquisition information management device and the sample acquisition information management system includes an image acquisition unit (16) that acquires an image and a video of a sample acquisition operation of a subject using a sample examination kit, an (Continued)

output unit (18) that outputs acquisition means information and operation check information, and a processing unit (20) that determines whether or not the image or the video acquired by the image acquisition unit (16) corresponds to a correct sample acquisition operation and controls display of the acquisition means information and the operation check information. Further, the sample acquisition information management method uses the sample acquisition information management system.

13 Claims, 17 Drawing Sheets

(51) Int. Cl.
*A61J 1/05* (2006.01)
*G02B 26/10* (2006.01)

(56) References Cited

U.S. PATENT DOCUMENTS

| | | | | |
|---|---|---|---|---|
| 2014/0081193 A1* | 3/2014 | Watters | ............... | A61M 1/3663 604/4.01 |
| 2015/0046183 A1* | 2/2015 | Cireddu | ................. | G16H 40/67 705/3 |
| 2015/0095717 A1* | 4/2015 | Frenz | ................... | G06F 11/2294 714/46 |
| 2016/0180743 A1* | 6/2016 | Ahmad | .................. | G09B 23/28 434/262 |
| 2019/0076064 A1 | 3/2019 | Tahara et al. | | |
| 2019/0183445 A1* | 6/2019 | Okuno | ...................... | A61B 6/12 |

FOREIGN PATENT DOCUMENTS

| | | | | |
|---|---|---|---|---|
| JP | 2003-116796 A | | 4/2003 | |
| JP | 2003-270239 A | | 9/2003 | |
| JP | 2007-535979 A | | 12/2007 | |
| JP | 2008-90465 A | | 4/2008 | |
| JP | 2013-235341 A | | 11/2013 | |
| JP | 2017188135 A | * | 10/2017 | |
| JP | 2018-19765 A | | 2/2018 | |
| JP | 2018-36351 A | | 3/2018 | |
| JP | 2018036351 A | * | 3/2018 | |
| WO | WO-2015016338 A1 | * | 2/2015 | ....... G01N 35/00584 |
| WO | WO-2017006962 A1 | * | 1/2017 | ....... A61B 5/150022 |
| WO | WO-2017006963 A1 | * | 1/2017 | ........... A61B 5/1405 |
| WO | WO 2018/021215 A1 | | 2/2018 | |

OTHER PUBLICATIONS

International Preliminary Report on Patentability and English translation of the Written Opinion of the International Searching Authority for International Application No. PCT/JP2019/012374, dated Oct. 8, 2020.

International Search Report for International Application No. PCT/JP2019/012374, dated Jun. 4, 2019.

Oda et al., "Monitoring system to prevent accidents for blood purification," IEICE Technical Report, vol. 108, No. 314, Nov. 14, 2008, pp. 7-10, 7 pages total, with an English abstract.

Sasajima et al., "A Study of Nursing Education IT: Thought of teaching side and learner side, and service design," Research report of Ubiquitous Computing System, vol. 2015-UBI-047, No. 15, Jul. 20, 2015, pp. 1-6, 8 pages total.

Japanese Office Action for corresponding Japanese Application No. 2020-510036, dated Jan. 24, 2022, with English translation.

Chinese Office Action and Search Report for corresponding Chinese Application No. 201980022044.5, dated Oct. 18, 2023, with English translation.

Chinese Office Action for corresponding Chinese Application No. 201980022044.5, dated Mar. 2, 2024, with English translation.

Chinese Office Action for Chinese Application No. 201980022044.5, dated Jun. 22, 2024, with an English translation.

* cited by examiner

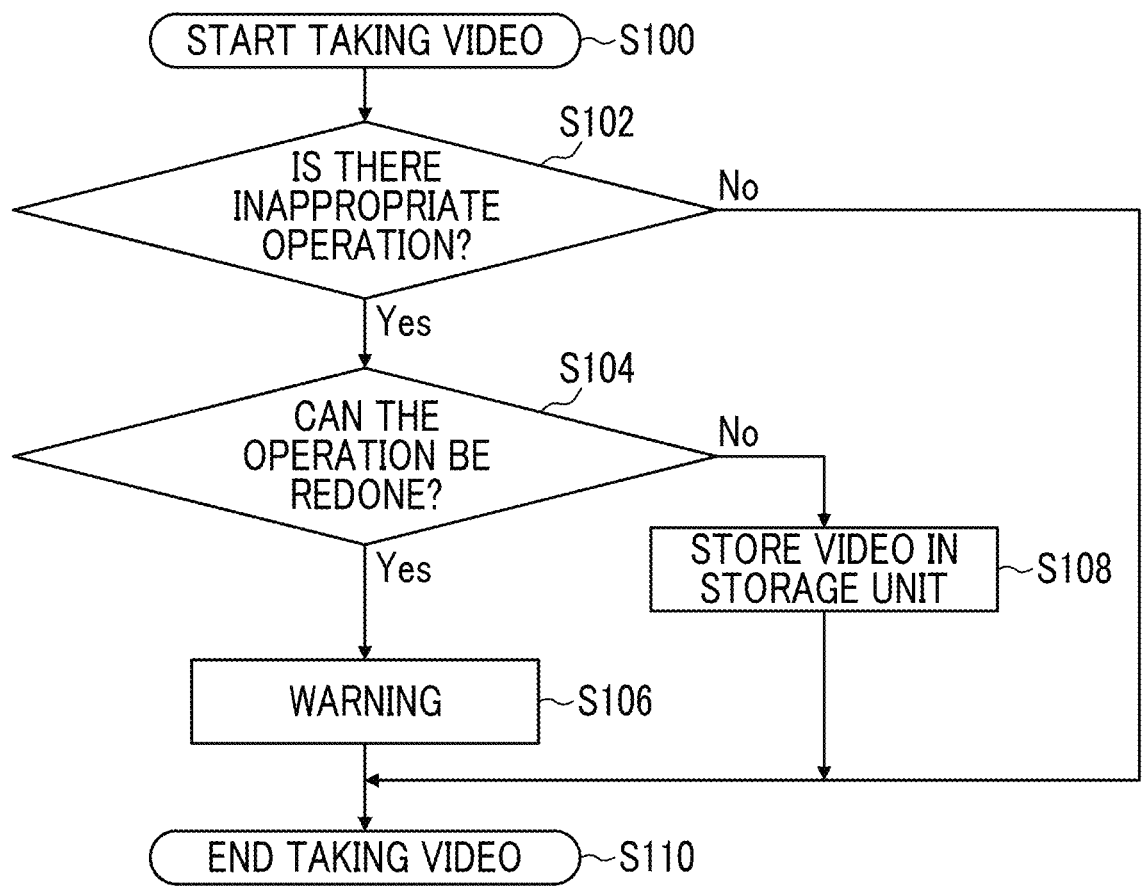

SAMPLE ACQUISITION INFORMATION MANAGEMENT DEVICE, SAMPLE ACQUISITION INFORMATION MANAGEMENT SYSTEM, AND SAMPLE ACQUISITION INFORMATION MANAGEMENT METHOD

CROSS-REFERENCE TO RELATED APPLICATIONS

The present application is a Continuation of PCT International Application No. PCT/JP2019/012374 filed on Mar. 25, 2019 claiming priority under 35 U.S.C. § 119(a) to Japanese Patent Application No. 2018-062721 filed on Mar. 28, 2018. Each of the above applications is hereby expressly incorporated by reference, in its entirety, into the present application.

BACKGROUND OF THE INVENTION

1. Field of the Invention

The present invention relates to a sample acquisition information management device, a sample acquisition information management system, and a sample acquisition information management method, and more particularly, to a sample acquisition information management device, a sample acquisition information management system, and a sample acquisition information management method that manage the sample acquisition information of a subject to be examined who collects a sample by oneself.

2. Description of the Related Art

Generally, the collection of blood includes: the general collection of blood where a person having a certain qualification, such as a medical doctor, collects blood from the vein using a syringe; and the self-collection of blood where a subject to be examined pricks the finger or the like of one's own hand with a blood collection needle and collects blood. Blood, which is collected through the collection of blood, is sent to a medical institution or an examination institution in a state where the blood is sealed in a collection container, and is examined there. In a case where blood is sent without being separated into blood cells and plasma, blood is examined after being separated into blood cells and plasma by a centrifugal separator in the medical institution or the examination institution. With regard to self-blood-collecting examination, for example, a service where a blood examination kit and a portable terminal (a smartphone or the like) are connected to each other so that self-blood-collecting examination can be simply performed is performed.

For example, JP2007-535979A to be described below discloses a sample material collection method including transmitting an instruction, which includes a sample collection procedure, to a hand-held device, determining whether or not the sample collection procedure is performed according to the instruction, and communicating a message about uncompleted collection in a case where the sample collection procedure is not performed.

SUMMARY OF THE INVENTION

In order to perform highly accurate analysis of self-collected blood, it is important that a subject reliably perform a blood collection operation. However, there is no method of checking the blood collection operation of the subject on an analysis side. Particularly, in a case where the amount of self-collected blood of the subject to be examined is not sufficient, there is a possibility that a re-examination cannot be made in such a blood examination kit in a case where a re-examination needs to be made. Accordingly, it is desired that the subject to be examined reliably performs a self-blood-collecting action.

The method disclosed in JP2007-535979A is a system for monitoring a blood collection sequence (sample collection procedure) in a hospital, and is not a system of monitoring a procedure for the self-collection of blood.

The invention has been made in consideration of the above-mentioned circumstances, and provides a sample acquisition information management device, a sample acquisition information management system, and a sample acquisition information management method that allow a subject who is to collect a sample by oneself to reliably perform a sample acquisition operation.

In order to achieve an object of the invention, a sample acquisition information management system according to an aspect of the invention comprises an image acquisition unit that acquires at least one of an image or a video of a sample acquisition operation of a subject using a sample examination kit, an output unit that outputs acquisition means information and operation check information, and a processing unit that determines whether or not the image or the video acquired by the image acquisition unit corresponds to a correct sample acquisition operation and controls display of the acquisition means information and the operation check information. The processing unit includes an output control section that delivers the acquisition means information according to a request of the subject, and stops delivering the acquisition means information and delivers the operation check information in a case where delivery of a predetermined sample acquisition operation of the acquisition means information ends, and a determination section that determines whether or not the image or the video acquired by the image acquisition unit corresponds to a normal sample acquisition operation.

According to the aspect of the invention, in the sample acquisition operation using the sample examination kit, an image or a video is acquired during the predetermined sample acquisition operation is performed and the determination section determines whether or not the image or the video corresponds to a normal sample acquisition operation. Then, the delivery of the acquisition means information and the operation check information is controlled on the basis of this determination, so that the subject repeats the sample acquisition operation until the check of the normal sample acquisition operation is removed. Accordingly, since the sample acquisition operation to be checked can be reliably performed, the mistake of the sample acquisition operation can be removed.

In an aspect of the invention, it is preferable that the output control section releases the stop of the delivery of the acquisition means information and resumes the delivery of the acquisition means information in a case where the determination section determines that the sample acquisition operation is normal during the sample acquisition operation, and the output control section delivers the operation check information again in a case where the determination section determines that the sample acquisition operation is abnormal.

According to this aspect, in a case where the determination section determines that the sample acquisition operation is normal, the output control section resumes the delivery of the acquisition means information and an operation proceeds to the next operation. In a case where the determination section determines that the sample acquisition operation is abnormal, the output control section delivers the operation check information again. Accordingly, an operation does not progress to the next operation until it is determined that the sample acquisition operation is a normal operation. Therefore, since the subject can reliably perform each predetermined sample acquisition operation, the subject can reliably perform a sample acquisition operation.

In an aspect of the invention, it is preferable that the operation check information is a request image for the sample acquisition operation and an image of a normal sample acquisition operation.

According to this aspect, since a request image for the sample acquisition operation and an image of a normal sample acquisition operation are used as the operation check information, the subject takes the image of one's own operation corresponding to a sample acquisition operation, of which the operation check information is delivered, and transmits the taken image. Further, since the image of a normal sample acquisition operation is delivered, it is possible to prevent the subject from transmitting the image of an abnormal sample acquisition operation. Accordingly, the sample acquisition operation can be smoothly performed.

In an aspect of the invention, it is preferable that the sample acquisition information management device further comprises an image storage section storing the image or the video acquired by the image acquisition unit.

According to this aspect, since the sample acquisition information management device includes the image storage section, the sample acquisition information management device can store the image or the video of the sample acquisition operation of the subject that is acquired by the image acquisition unit. Accordingly, the image of a normal operation that is performed by oneself or an image that is determined to be abnormal can be displayed during the next and subsequent sample acquisition operations. Further, a person other than the subject, such as an analyzer, can check whether or not the sample acquisition operation has been normally performed after the acquisition of a sample.

In an aspect of the invention, it is preferable that the sample examination kit has a unique kit ID for each sample examination kit and the image storage section stores the image or the video acquired by the image acquisition unit and the kit ID so that the image or the video and the kit ID are associated with each other.

According to this aspect, since the sample examination kit has a unique kit ID and the image or the video and the kit ID are stored in association with each other, the image and the video of the subject can be easily found.

In an aspect of the invention, it is preferable that the output control section outputs warning information from the output unit in a case where the determination section recognizes that the video acquired by the image acquisition unit corresponds to an abnormal operation of the subject.

According to this aspect, since the output control section outputs warning information in a case where the determination section recognizes that the sample acquisition operation is an abnormal operation from the acquired video, the subject can notice that an operation being performed now by oneself is not appropriate. Accordingly, the subject redoes the sample acquisition operation with an appropriate operation, so that the subject can reliably acquire a sample.

In an aspect of the invention, it is preferable that the sample examination kit is a self-blood-collecting examination kit and includes a lancet used to puncture a skin, a blood collection instrument including a fiber rod, a storage instrument containing a diluent therein, a cylinder including a separation instrument for separating plasma and a blood cell, and a cap including a sealing member.

The sample acquisition information management device according to the aspect of the invention can be preferably used for a blood collection operation that uses a self-blood-collecting examination kit as a sample examination kit to be used by the subject.

In an aspect of the invention, it is preferable that the sample acquisition operation includes at least one of a state where the fiber rod has absorbed blood, a state where the fiber rod is dropped into the storage instrument and the storage instrument is shaken, a state where the separation instrument provided at a distal end of the cylinder reaches a bottom of the storage instrument, or a state where the sealing member provided at the cap is inserted.

According to this aspect, in a case where the above-mentioned state is reliably performed, a sufficient amount of blood can be acquired as a blood sample for analysis or hemolysis can be prevented.

In an aspect of the invention, it is preferable that the output control section outputs warning information from the output unit in a case where the determination section recognizes that the video acquired by the image acquisition unit corresponds to an abnormal operation of the subject, and the warning information is output in at least one of a case where a position pricked with the lancet is not a distal end portion of a finger, a case where the subject is to drop the fiber rod having absorbed blood into a portion other than the storage instrument, a case where the subject is to close the cap without inserting the cylinder into the storage instrument, or a case where a cold insulation material is not set in a post container.

According to this aspect, in a case where the above-mentioned operation is performed as an operation where the warning information is output, the subject can interrupt the above-mentioned operation and redo the above-mentioned operation. Accordingly, the subject can perform an appropriate sample acquisition operation, so that the subject can reliably collect blood.

In an aspect of the invention, it is preferable that the sample acquisition information management device further comprises an image storage section storing the image or the video acquired by the image acquisition unit, the sample examination kit has a unique kit ID for each sample examination kit, and the image storage section stores the video and the kit ID so that the video and the kit ID are associated with each other, in a case where the determination section determines that the video acquired by the image acquisition unit corresponds to at least one of a case where the diluent present in the storage instrument is spilled or a case where the unused lancet is not recovered.

According to this aspect, in a case where the determination section determines that the acquired video corresponds to the above-mentioned state, the video and the kit ID are stored in the storage unit in association with each other. In a case where the diluent is spilled, an accurate analysis cannot be made and it is difficult for the determination section to determine that an operation is a normal operation during the check of the sample acquisition operation. Accordingly, there is a case where the acquisition means information is not delivered. Since the video is stored in association with the kit ID, the video can be checked later. Since the sample examination kit needs to be treated as medical waste, the sample examination kit can be checked later in a case where the video and the kit ID are stored in association with each other even though an unused lancet does not need to be recovered.

In order to achieve an object of the invention, a sample acquisition information management system according to an aspect of the invention comprises a server device that is adapted to be connectable to a terminal through a network; the server device includes an image acquisition unit that acquires at least one of an image or a video of a sample acquisition operation of a subject using a sample examination kit, an output unit that outputs acquisition means information and operation check information, and a processing unit that determines whether or not the image or the video acquired by the image acquisition unit corresponds to a correct sample acquisition operation and controls display of the acquisition means information and the operation check information; and the processing unit includes an output control section that delivers the acquisition means information according to a request of the subject, and stops delivering the acquisition means information and delivers the operation check information in a case where a predetermined sample acquisition operation is performed, and a determination section that determines whether or not the image or the video acquired by the image acquisition unit is normal.

According to the aspect of the invention, in the sample acquisition operation using the sample examination kit, an image or a video is acquired during the predetermined sample acquisition operation is performed and the determination section determines whether or not the image or the video corresponds to a normal sample acquisition operation. Then, the delivery of the acquisition means information and the operation check information is controlled on the basis of this determination, so that the subject repeats the sample acquisition operation until the check of the normal sample acquisition operation is removed. Accordingly, since the sample acquisition operation to be checked can be reliably performed, the mistake of the sample acquisition operation can be removed.

In an aspect of the invention, it is preferable that the terminal is a portable terminal of the subject.

According to this aspect, since a case where a portable terminal of the subject is used as the terminal, the subject oneself requests the acquisition means information from one's own portable terminal and can easily acquire a sample on the basis of the acquisition means information.

In an aspect of the invention, it is preferable that the terminal comprises a display unit displaying the acquisition means information and the operation check information and an imaging unit taking the image and the video of the sample acquisition operation.

According to this aspect, since the terminal comprises the display unit and the imaging unit, the subject can simply acquire a sample according to an instruction given from the terminal.

In order to achieve an object of the invention, a sample acquisition information management method according to an aspect of the invention, which uses a sample acquisition information management system including a server device that is adapted to be connectable to a terminal through a network, comprises: a step of causing an output control section to deliver acquisition means information according to a request of a subject and to cause a display unit of the terminal to display the acquisition means information; a step of causing the output control section to stop delivering the acquisition means information, to deliver operation check information, and to cause the display unit of the terminal to display the operation check information in a case where a predetermined sample acquisition operation is performed; a step of causing an image acquisition unit to acquire at least one of an image or a video of a sample acquisition operation of the subject using an examination kit; a step of causing a determination section to determine whether or not the image or the video corresponds to a normal sample acquisition operation; and a step of causing the output control section to release the stop of the delivery of the acquisition means information and to resume the delivery of the acquisition means information in a case where the determination section determines that the sample acquisition operation is normal and causing the output control section to deliver the operation check information again in a case where the determination section determines that the sample acquisition operation is abnormal.

According to the aspect of the invention, the image or the video of the sample acquisition operation of the subject is acquired during the acquisition of a predetermined sample, and the determination section determines whether or not the image or the video corresponds to a normal sample acquisition operation. After the determination section determines that the image or the video corresponds to a normal sample acquisition operation, the operation progresses to the next procedure. In a case where the determination section determines that the image or the video corresponds to an abnormal sample acquisition operation, the output control section delivers the operation check information again. Accordingly, since the operation progresses to the next procedure only in a case where it is checked that the image or the video corresponds to a normal operation, the subject can check an appropriate operation for each predetermined operation of the sample acquisition operation. Therefore, the subject can reliably acquire a sample.

Since the sample acquisition information management device according to the aspect of the invention comprises the processing unit including the determination section that determines whether or not the image or the video acquired by the image acquisition unit corresponds to a normal sample acquisition operation, the subject can collect a sample by oneself while checking that an operation is a normal sample acquisition operation. Accordingly, the subject can reliably collect a sample by oneself on the basis of a normal sample acquisition operation.

BRIEF DESCRIPTION OF THE DRAWINGS

FIG. 17 is a flowchart of a work check step using a video.

DESCRIPTION OF THE PREFERRED EMBODIMENTS

A sample acquisition information management device, a sample acquisition information management system, and a sample acquisition information management method according to embodiments of the invention will be described below with reference to the accompanying drawings. In this specification, a numerical range expressed using "to" means a range that includes numerical values written on the front and rear of "to" as a lower limit and an upper limit. A standard component constantly present in blood is referred to as an external standard material or an external standard. Further, a standard component not present in blood is referred to as an internal standard material or an internal standard.

[Overall Configuration of Sample Acquisition Information Management System]

Figure 1:
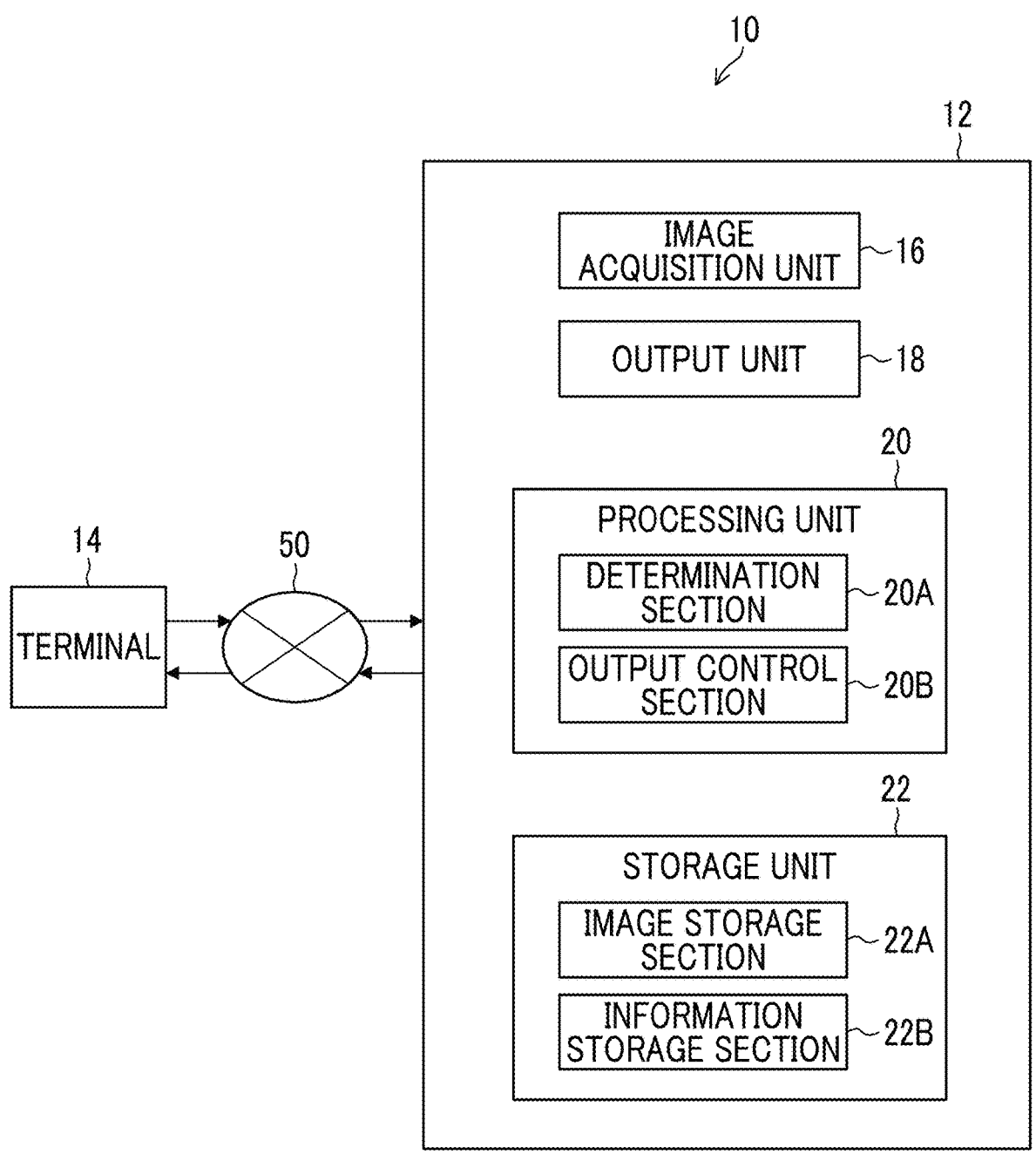
FIG. 1 is a block diagram showing an example of the configuration of a sample acquisition information management system.

FIG. 1 is a block diagram showing an example of the configuration of a sample acquisition information management system. The sample acquisition information management system 10 shown in FIG. 1 comprises a server device 12 and a terminal 14. The server device 12 and the terminal 14 are connected to each other through a network 50 so that data communication can be performed. The server device 12 corresponds to an example of the sample acquisition information management device. A publicly known standard can be applied to the data communication.

The terminal 14 is a terminal device that is to be operated by a subject (a person who is to collect a sample). Examples of the terminal 14 include a computer, such as a personal computer, a portable terminal, such as a smartphone, and the like. These may be a computer, a portable terminal, and the like that are possessed by the subject.

The server device 12 comprises an image acquisition unit 16, an output unit 18, a processing unit 20, and a storage unit 22. The image acquisition unit 16 acquires the image or the video of a sample acquisition operation that is taken by the subject. The output unit 18 outputs acquisition means information and operation check information. The acquisition means information includes a video or the like that shows a procedure for acquiring a sample. Further, the operation check information includes a request image used to request the image or the video of the sample acquisition operation of the subject, the image of a normal sample acquisition operation, and the like in a case where a predetermined sample acquisition operation is performed.

The processing unit 20 comprises a determination section 20A that determines whether or not the image acquired by the image acquisition unit 16 corresponds to a correct sample acquisition operation, and an output control section 20B that performs the control of the display of the acquisition means information and the operation check information, that is, the delivery and stop of the acquisition means information and the delivery and stop of the operation check information.

The storage unit 22 comprises an image storage section 22A that stores the image or the video acquired by the image acquisition unit 16. Further, the storage unit 22 includes an information storage section 22B that stores the acquisition means information and the operation check information to be output from the output unit 18.

[Function of Sample Acquisition Information Management System]

Figure 2:
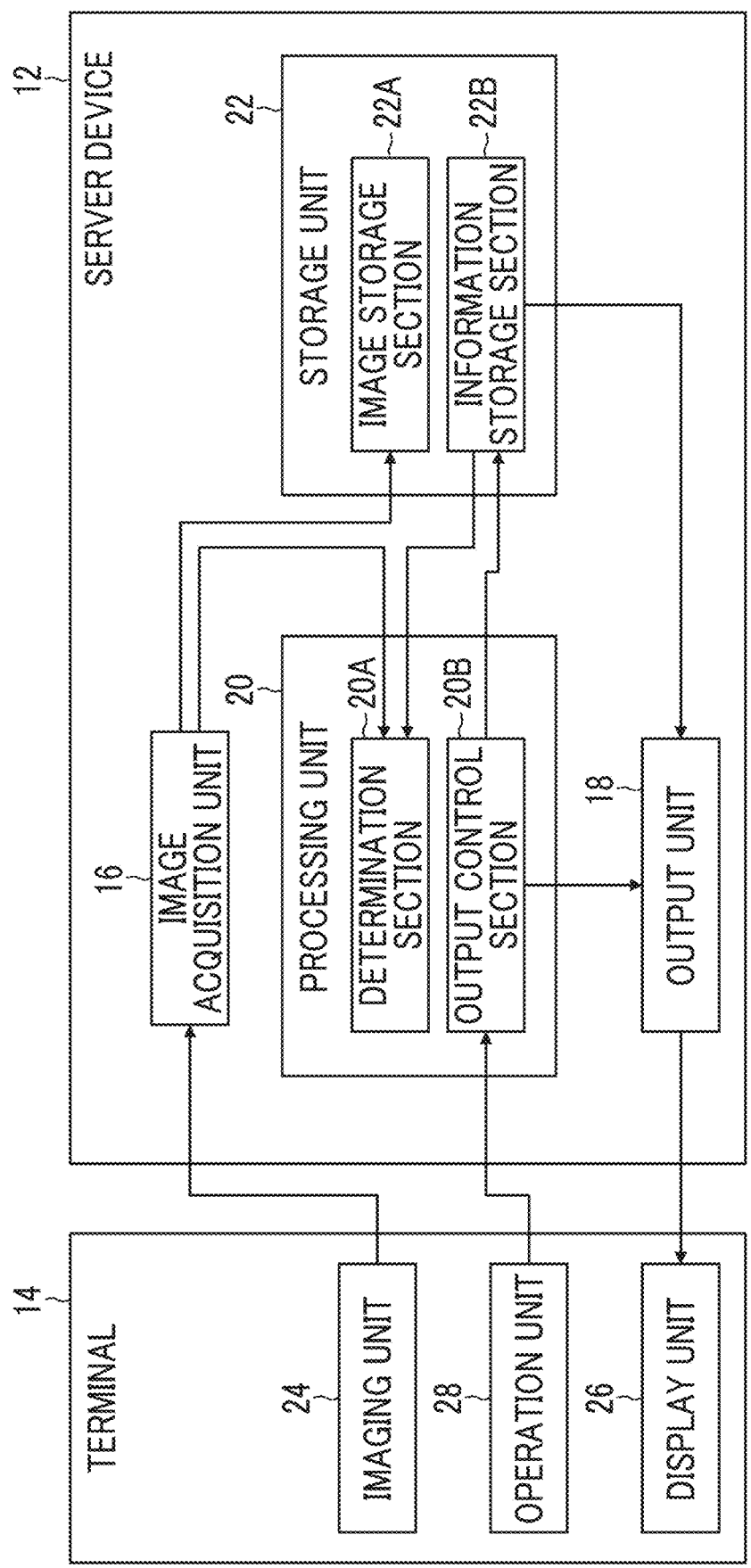
FIG. 2 is a functional block diagram of a server device and a terminal.

FIG. 2 is a functional block diagram of the server device and the terminal. The server device 12 shown in FIG. 2 comprises the image acquisition unit 16, the output unit 18, the processing unit 20, and the storage unit 22. Further, the terminal 14 comprises an imaging unit 24, a display unit 26, and an operation unit 28. The details of each unit will be described below.

<Image Acquisition Unit>

The image acquisition unit 16 acquires the image and the video of the sample acquisition operation of the subject (a person who is to collect a sample) that is taken by the terminal 14. Hardware can be applied as the image acquisition unit 16, and examples of the configuration of the hardware include configuration that comprises a signal input element, a signal conversion element, and the like.

Examples of the image acquired by the image acquisition unit 16 include the image of the sample acquisition operation that is performed by the subject on the basis of the request image requested as the operation check information output from the output unit 18.

Further, examples of the video acquired by the image acquisition unit 16 include the video of the sample acquisition operation that is performed by the subject. The video may continue to be taken until the sample acquisition operation ends after being started, or may be taken from an operation that is desired to be checked by the subject.

The video or the image acquired by the image acquisition unit 16 is stored in the image storage section 22A of the storage unit 22.

<Output Unit>

The output unit 18 outputs the acquisition means information and the operation check information. The acquisition means information and the operation check information are stored in the information storage section 22B of the storage unit 22. The acquisition means information and the operation check information output from the output unit 18 can be acquired by the terminal 14, and are displayed by the display unit 26 of the terminal 14.

<Processing Unit>

The processing unit 20 comprises the determination section 20A that determines whether or not the image or the video acquired by the image acquisition unit 16 corresponds to a correct sample acquisition operation, and the output control section 20B that performs the delivery and stop of the acquisition means information and the delivery of the operation check information.

(Determination Section)

The determination section 20A acquires the image of the sample acquisition operation of the subject through the image acquisition unit 16. Further, the determination section 20A acquires a normal operation image of a corresponding sample acquisition operation from the information storage section 22B. The determination section 20A compares the image of the sample acquisition operation of the subject with the normal operation image to determine whether or not the image acquired by the image acquisition unit 16 corresponds to a normal sample acquisition operation.

Further, the determination section 20A acquires the video of the sample acquisition operation of the subject through the image acquisition unit 16. Furthermore, the determination section 20A acquires the image or the video of a corresponding sample acquisition operation from the information storage section 22B. The determination section 20A determines whether or not a corresponding sample acquisition operation is normally performed in the video of the sample acquisition operation of the subject.

In a case where it takes time to acquire the image or the video of the sample acquisition operation of the subject after the operation check information is delivered, the determination section 20A determines that the subject has no or less experience in the sample acquisition operation.

(Output Control Section)

The output control section 20B controls the delivery of the acquisition means information and the operation check information to the terminal 14 through the output unit 18.

The output control section 20B instructs the output unit 18 to deliver the acquisition means information according to the request of the subject. The output unit 18 acquires the acquisition means information from the information storage section 22B and delivers the acquisition means information to the display unit 26 of the terminal 14.

The output control section 20B stops the delivery of the acquisition means information at a point of time when the delivery of a predetermined sample acquisition operation ends in the middle of the delivery of the acquisition means information from the output unit 18. The output control section 20B stops the delivery of the acquisition means information, acquires the operation check information from the information storage section 22B, and delivers the operation check information to the display unit 26 of the terminal 14. It is preferable that the predetermined sample acquisition operation is an operation for ensuring the amount of a component, which is an object to be analyzed, such as a step relating to the amount of a collected sample or a step of managing a component of a sample. It is possible to ensure the amount of a component required for analysis by checking the operation of this step.

The output control section 20B releases the stop of the delivery of the acquisition means information and redisplays the operation check information on the basis of a result that is obtained in a case where the determination section 20A determines the image or the video acquired by the image acquisition unit 16. Specifically, in a case where the determination section 20A determines that the sample acquisition operation is appropriate (normal), the output control section releases the stop of the delivery of the acquisition means information and resumes the delivery of the acquisition means information. In a case where the determination section 20A determines that the sample acquisition operation is not appropriate (not normal), the output control section redisplays the operation check information.

Further, in a case where the determination section 20A determines that the sample acquisition operation is not normally performed in the determination using the video of the sample acquisition operation, warning information is output to the terminal 14 through the output unit 18.

Furthermore, in a case where the determination section 20A determines that a sample cannot be acquired from the video of the sample acquisition operation of the subject, such as a case where there is an action that cannot acquire an analyzable sample, the output control section 20B may deliver the acquisition means information even though it is not determined that the sample acquisition operation is a normal operation. In this case, it is prevented that the stop of the delivery of the acquisition means information is not released since it is difficult to perform a normal sample acquisition operation.

Further, in a case where the determination section 20A determines that it takes time to perform the sample acquisition operation since the subject has no or less experience in the collection of a sample, the output control section 20B reduces the display speed of the acquisition means information and controls the delivery of the acquisition means information so that the acquisition means information is displayed according to the operation time of the subject.

<Storage Unit>

The storage unit 22 includes the image storage section 22A that stores the image and the video acquired by the image acquisition unit 16, and the information storage section 22B that stores the acquisition means information and the operation check information to be delivered to the terminal 14. The storage unit may be included in the server device 12 as shown in FIG. 1, or may be provided separately from the server device 12 so that data communication can be performed.

(Image Storage Section)

The image storage section 22A stores the image and the video that are acquired by the image acquisition unit 16. The image and the video can be stored in association with a unique kit identification (ID) of each sample examination kit that is used by the subject to acquire a sample. The image and the video to be stored are not particularly limited. However, in a case where an image, which is determined to correspond to a normal operation by the determination section 20A, is stored, an analyzer can check whether the determination of the determination section is correct or not during an analysis. Further, in a case where an abnormal image is stored, the output unit 18 can also output the stored abnormal image of the subject in a case where the output unit 18 is to output the operation check information.

Furthermore, the image storage section 22A can store a video, which is obtained in a case where the determination section 20A determines that a sample cannot be acquired, as an abnormal action in association with a kit ID.

(Information Storage Section)

The information storage section 22B stores the acquisition means information and the operation check information. The acquisition means information includes a video showing a procedure for acquiring a sample or a plurality of images arranged according to the procedure, character information indicating instructions or cautions, and the like. Further, the operation check information includes a request image used to request the image or the video of a sample acquisition operation of a subject, the image of a normal sample acquisition operation, character information indicating instructions or cautions, and the like in a case where a predetermined sample acquisition operation is performed. The image of a typical failure example of the sample acquisition operation may be stored as the operation check information. In a case where the operation check information is output, the image of a failure example can be delivered to call attention.

<Imaging Unit>

The imaging unit 24 takes the image or the video of the sample acquisition operation of the subject. Examples of the imaging unit 24 include a camera or a video recorder provided in the terminal 14, and the like. Further, the imaging unit 24 is provided in the terminal 14 in FIG. 2, but a device for taking a video or an image may be provided separately from the terminal 14.

<Display Unit>

The display unit 26 displays the acquisition means information and the operation check information output through the output unit 18. Examples of the display unit 26 include a monitor.

<Operation Unit>

The operation unit 28 is a device that is to be operated by the subject, and is formed of a touch panel or the like in a case where the terminal 14 is a portable terminal. Further, in a case where the terminal 14 is a computer, the operation unit 28 is formed of a keyboard, a mouse, and the like. The contents to be input through the operation unit 28 includes: a request for the delivery of the acquisition means information; the transmission of the image or the video, which is taken by the imaging unit, to the server device 12; and the unique kit ID of a sample examination kit, and the like.

<Procedure of Sample Acquisition Information Management Method>

Next, a procedure of the sample acquisition information management method will be described. A method using a self-blood-collecting examination kit for collecting blood as a sample will be described as an example of the sample acquisition information management method. A sample examination kit is not limited to the self-blood-collecting examination kit, and can be used for a self-examination kit that is used for examination where a subject collects a sample by oneself. Examples of the sample include urine, nasal mucus, saliva, stool, and the like.

[Self-Blood-Collecting Examination Kit]

Figure 3:
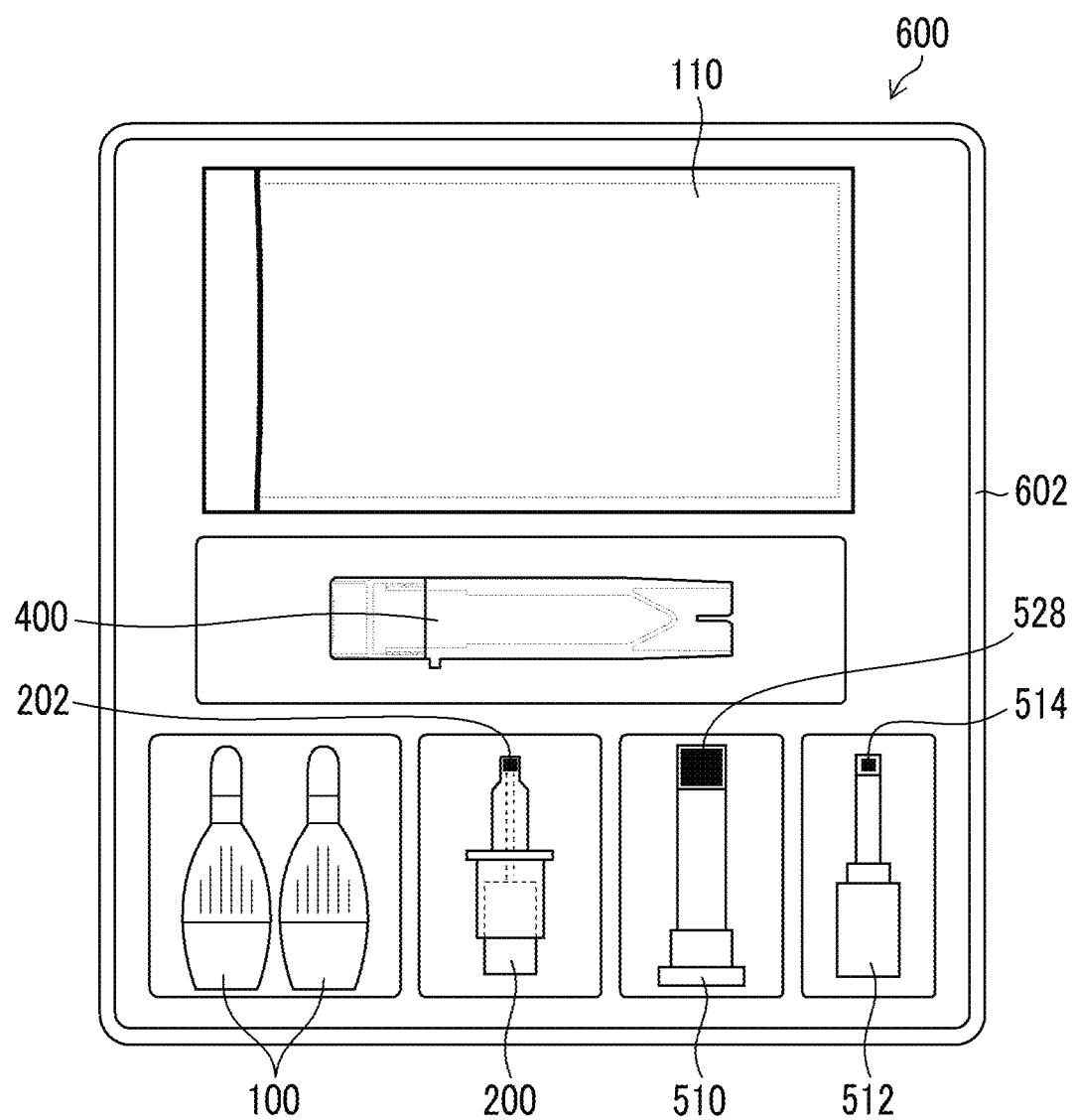
FIG. 3 is a diagram showing the configuration of an example of a self-blood-collecting examination kit.

First, the self-blood-collecting examination kit will be described. A biological sample-separation instrument disclosed in, for example, JP2003-270239A can be used as a specific example of the self-blood-collecting examination kit. FIG. 3 is a diagram showing the configuration of an example of the self-blood-collecting examination kit. The self-blood-collecting examination kit 600 shown in FIG. 3 comprises publicly known lancets 100 corresponding to a blood collection needle and a blood collection instrument 200 for collecting blood, in addition to a cap 512 provided with a sealing member 514, a cylinder 510, and a storage instrument 400 containing a diluent which are included in the biological sample-separation instrument. Further, the self-blood-collecting examination kit 600 comprises a packaging container 110 that is used to package a liquid sample-collecting pipe containing collected blood to send the liquid sample-collecting pipe by post. Two lancets 100 are provided in FIG. 3. One lancet is a spare lancet, and is provided to cause bleeding again in a case where a sufficient amount of blood cannot be obtained from one time of puncture with a lancet.

The cap 512, the cylinder 510, the blood collection instrument 200, the lancets 100, the storage instrument 400, and the packaging container 110 are housed in a case 602. The self-blood-collecting examination kit 600 may comprise an adhesive plaster and a disinfecting cloth or an instruction manual (not shown). Further, the self-blood-collecting examination kit 600 may comprise a simple stand (paper assembly) for standing a portable terminal so that an image is easily taken in a case where an image is to be acquired.

The respective components of the self-blood-collecting examination kit 600 will be described below.

[Storage Instrument]

Figure 4:
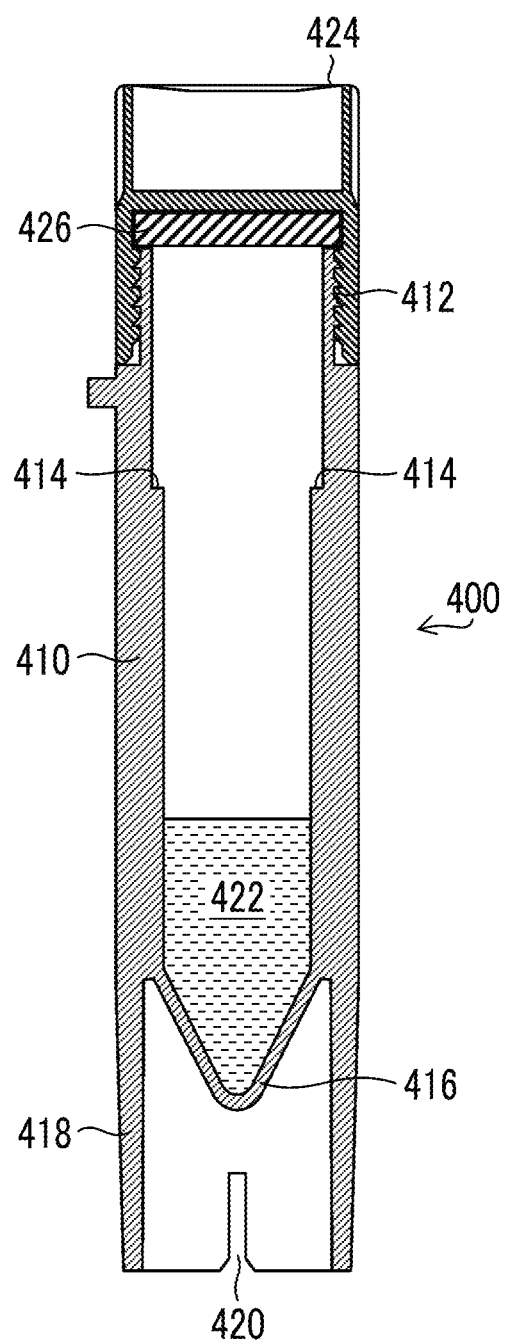
FIG. 4 is a diagram showing an example of the configuration of a storage instrument for storing a dilution of a blood sample.

FIG. 4 is a cross-sectional view showing an example of the configuration of the storage instrument for storing a dilution of a blood sample. As shown in FIG. 4, the storage instrument 400 includes a cylindrical blood collection container 410 made of a transparent material. A threaded portion 412 is formed on the outer surface of an upper end portion of the blood collection container 410, and a locking portion 414 protrudes from the inner surface of the blood collection container 410. Further, a conical bottom portion 416, which protrudes toward the lower end, is formed at the lower end portion of the blood collection container 410. A cylindrical leg portion 418 is formed around the bottom portion 416. "Upper" and "lower" mean "upper" and "lower" in a state where the leg portion 418 is installed on a placement surface.

The leg portion 418 has the same outer diameter as a sample cup (not shown) that is used for the analysis and examination of blood, and it is preferable that slit grooves 420 are formed at positions facing each other on the lower end of the leg portion 418 so as to extend in a vertical direction. In addition, it is preferable that a required amount, for example, 500 mm$^3$ of a diluent 422 is stored in the blood collection container 410 as shown in FIG. 4.

It is preferable that an upper end opening of the blood collection container 410 is sealed by a cap 424 through a packing 426 as shown in FIG. 4 before the storage instrument 400 is used.

[Standard Component Constantly Present in Blood]

A method of obtaining the rate of change of the concentration of a material, which is present in a diluent in advance, can be employed to accurately analyze the concentration of a diluted target component, which is present in the plasma of blood not yet diluted, of diluted plasma having a high dilution factor of a plasma component. Further, a method of analyzing the concentration of a target component of a blood sample using a standard component constantly present in blood can also be employed. In a case where a blood component is to be analyzed from a smaller amount of blood, it is preferable to employ a method using a standard component constantly present in blood since measurement with a small measurement error can be performed. Accordingly, a method of analyzing the concentration of a target component of a blood sample using a standard component constantly present in blood is one of preferred aspects.

Here, "using" a standard component means that a dilution factor used to analyze the concentration of a target component is determined on the basis of the standard value of the standard component (a constant value in a case where the standard component constantly present in blood is used). Accordingly, in a case where the concentration of a target component of a blood sample is to be analyzed using the standard component constantly present in blood, a dilution factor is determined on the basis of the constant value (standard value) of the standard component constantly present in blood and the concentration of the target component is analyzed.

Examples of the standard component constantly present in blood include a sodium ion, a chloride ion, a potassium ion, a magnesium ion, a calcium ion, total protein, albumin, and the like. With regard to the concentrations of these standard components to be contained in the serum and the plasma of a blood sample, the concentration of a sodium ion is in the range of 134 mmol/L to 146 mmol/L (average value: 142 mmol/L), the concentration of a chloride ion is in the range of 97 mmol/L to 107 mmol/L (average value: 102 mmol/L), the concentration of a potassium ion is in the range of 3.2 mmol/L to 4.8 mmol/L (average value: 4.0 mmol/L), the concentration of a magnesium ion is in the range of 0.75 mmol/L to 1.0 mmol/L (average value: 0.9 mmol/L), the concentration of a calcium ion is in the range of 4.2 mmol/L to 5.1 mmol/L (average value: 4.65 mmol/L), the concentration of total protein is in the range of 6.7 g/100 ml to 8.3 g/100 ml (average value: 7.5 g/100 mL), and the concentration of albumin is in the range of 4.1 g/100 mL to 5.1 g/100 mL (average value: 4.6 g/100 mL). In order relieve the pain of a subject, the embodiment is to allow a target component to be measured in a case where the amount of blood to be collected is very small. In a case where a small amount of blood is diluted with a diluent, the concentration of "the standard component constantly present in blood" present in the diluent needs to be accurately measured. In a case where a dilution factor is increased, the concentration of a component, which has been originally present in blood, in the diluent is lowered and there is a possibility that a measurement error is included depending on the dilution factor during the measurement of the concentration. Accordingly, in a case where a small amount of blood component is diluted with a high dilution factor, it is preferable to measure a standard component present at a high concentration in a small amount of blood to sufficiently accurately detect the standard component. In the invention, it is preferable that a sodium ion (Nat) or a chloride ion (CO present at a high concentration is used among the components constantly present in a blood sample. In addition, it is most preferable to measure a sodium ion of which the amount present in blood is largest among the above-mentioned standard components constantly present in blood. The average value of the concentration of a sodium ion is a standard value (the median of a reference range), is 142 mmol/L, and a sodium ion accounts for 90 mol % or more of the total cations contained in plasma.

[Standard Component not Present in Plasma]

A self-blood-collecting examination kit, which is used to analyze the concentration of a target component of a blood sample using a standard component not present in blood, may be provided as another aspect. This self-blood-collecting examination kit may be a kit that uses the standard component not present in blood together with the standard component constantly present in blood, and may be a kit that uses only the standard component not present in blood without using the standard component constantly present in blood.

In both the cases, the standard component not present in blood can be used and added to a diluent to be described later so as to have predetermined concentrations. A material, which is not contained in a blood sample at all or is contained in a blood sample by a very small amount even if being contained, can be used as the standard component not present in blood. As the standard component not present in blood, it is preferable to use a material that does not interfere with the measurement of a target component of a blood sample, a material that is not decomposed by the action of biological enzymes of a blood sample, a material that is stable during dilution, a material that does not penetrate a blood cell membrane and is not contained in a blood cell, a material that is not adsorbed on a storage container for a buffer solution, and a material for which a detection system for being capable of performing accurate measurement can be used.

A material, which is stable even though the material is stored for a long time in a state where the material is added to a diluent, is preferable as the standard component not present in blood. Examples of the standard component not present in blood include glycerol triphosphate.

A second reagent is added in the case of the measurement of concentration after the dilution of blood to cause these standard components, which are not present in blood, to develop colors, and the concentrations of these standard components in the diluted blood can be obtained from the densities of the colors. For example, with regard to the measurement of glycerol triphosphate added to a diluent, a large amount of sample can be easily measured with a small amount of sample by an automatic biochemistry analyzer using the measurement of the concentration of the color of a coloring agent developed by oxidation condensation that is described in, for example, "Home medical revolution" (clinical examination Vol. 59, p. 397, 2015), which is a known document.

[Diluent]

The self-blood-collecting examination kit includes a diluent that is used to dilute a collected blood sample. In a case where the self-blood-collecting examination kit is a kit used to analyze the concentration of a target component of a blood sample using the standard component constantly present in blood, the diluent does not contain the standard component constantly present in blood. "Not contain" means "substantially not contain". Here, "substantially not contain" means a case where a constant material to be used to obtain a dilution factor is not contained at all or is contained at a concentration corresponding to a very small amount not affecting the measurement of the constant material of a diluent after the dilution of a blood sample even if being contained. In a case where a sodium ion or a chloride ion is used as the standard component constantly present in blood, a diluent substantially not containing a sodium ion or a chloride ion is used as the diluent.

The pH of blood of a healthy person is generally constantly maintained in the range of about pH7.30 to pH7.40. Accordingly, in order to prevent the decomposition or denaturation of a target component, it is preferable that the diluent is a buffer solution having a buffering action in the pH range of pH6.5 to pH8.0, preferably in the pH range of pH7.0 to pH7.5, and more preferably in the pH range of pH7.3 to pH7.4 and it is preferable that the diluent is a buffer solution containing a buffer component for suppressing a change in pH. These buffer solutions can be selected from buffer solutions substantially not containing a sodium ion or a chloride ion.

A chelating agent, a surfactant, an antibacterial agent, a preservative, a coenzyme, a saccharide, and the like may be contained in the buffer solution to maintain an analysis target component stable. Examples of the chelating agent include ethylenediaminetetraacetic acid (EDTA) salt, citric salt, oxalic acid salt, and the like. Examples of the surfactant include a cationic surfactant, an anionic surfactant, an amphoteric surfactant, and a nonionic surfactant. Examples of the preservative include sodium azide, an antibiotic, and the like. Examples of the coenzyme include pyridoxal phosphate, magnesium, zinc, and the like. Examples of the saccharide of an erythrocyte stabilizing agent include mannitol, dextrose, oligosaccharide, and the like. Particularly, in a case where an antibiotic is added, it is possible to suppress the growth of bacteria partially mixed from the surface of a finger during the collection of blood from the finger, to suppress the decomposition of biological components caused by bacteria, and to stabilize biological components.

The buffer solution also contains the standard component not present in blood in the self-blood-collecting examination kit that is used to analyze a target component using a standard component not present in the blood. It is also important that an internal standard material to be described later is not contained and a measurement system for blood analysis does not interfere.

From the viewpoint of diluting whole blood, it is possible to prevent the hemolysis of blood cells by making the osmotic pressure of the buffer solution be equal to or higher than that of blood (285 mOsm/kg (here, mOsm/kg represents the osmotic pressure of 1 kg of water of a solution and represents the number of millimoles of ions)). The osmotic pressures can be adjusted to be isotonic with each other by salts, a saccharide, a buffering agent, or the like that does not affect the measurement of a target component and the measurement of the standard component constantly present in blood. The osmotic pressure of the buffer solution can be measured by an osmometer.

In a case where the examination of a specific organ or a specific disease, such as a liver function, a kidney function, or metabolism, is performed as a blood test, a plurality of target components to be measured are generally analyzed at the same time to obtain information about the plurality of target components to be measured, which are specific to the organ or the disease, and to predict the state of the organ, a lifestyle habit, and the like. For example, the concentrations of several types of materials, such as alanine transaminase (ALT), aspartate aminotransferase (AST), γ-glutamyl transpeptidase (γ-GTP), alkaline phosphatase (ALP), total bilirubin, total protein, and albumin, in the blood are generally measured to examine the state of the liver. In order to measure the plurality of target components from one blood sample as described above, a certain amount of diluted blood is required in consideration of a possibility of remeasurement. Accordingly, it is important to ensure a certain amount of a diluent that is used to dilute collected blood. However, considering that the invasiveness of the subject is kept as low as possible, the amount of collected blood is very small. Accordingly, a dilution factor becomes a large factor of 7 or more.

(Blood Collection Instrument)

Figure 5:
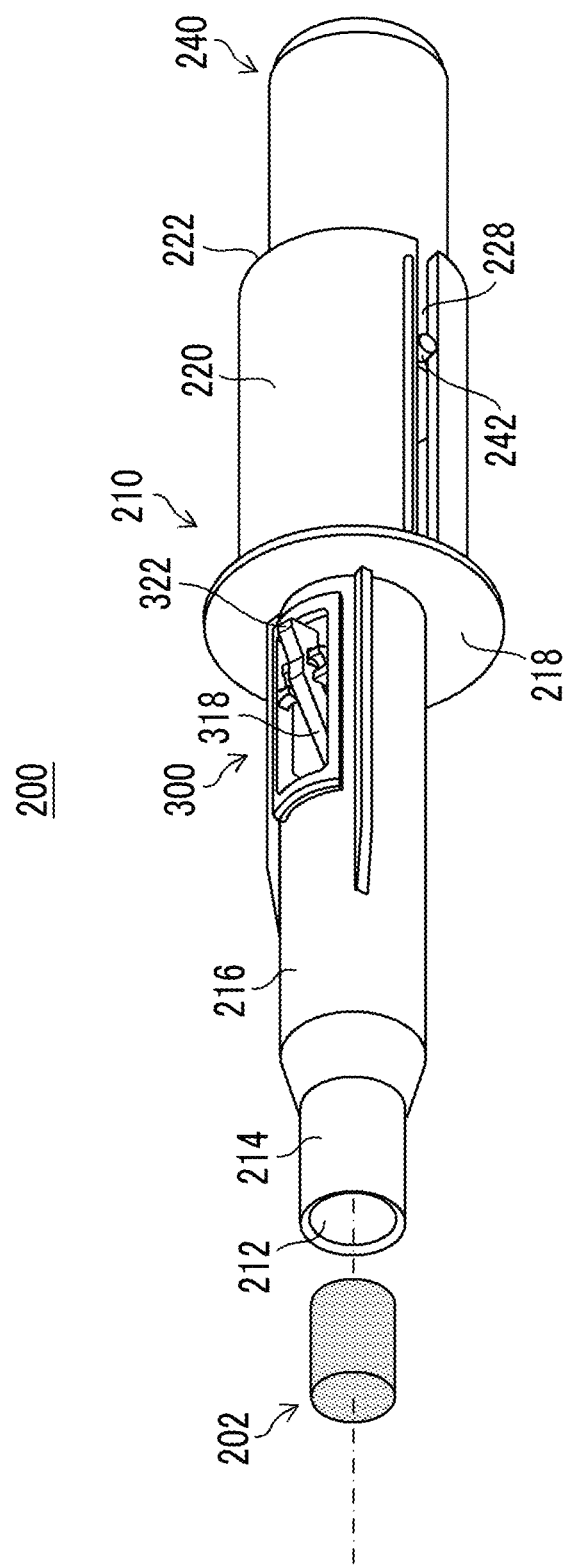
FIG. 5 is a diagram showing an example the configuration of a blood collection instrument.

FIG. 5 is a perspective view of the blood collection instrument 200. As shown in FIG. 5, the blood collection instrument 200 comprises a case 210 that includes an opening 212 defined on one side thereof and a fiber rod 202 that is attachably and detachably held on the side corresponding to the opening 212. The case 210 comprises a distal end-storage portion 214 storing the fiber rod 202, a middle portion 216, a flange portion 218, and a proximal end-storage portion 220 that are arranged toward the other side from the opening 212. The proximal end-storage portion 220 includes an opening 222, and a push rod 240 is inserted into the proximal end-storage portion 220 from the opening 222. The case 210 is an integrated molding, and the openings 212 and 222 communicate with each other.

The fiber rod 202 is attachably and detachably held by the distal end-storage portion 214. The middle portion 216 includes a lock lever 300. The push rod 240 includes an opening (not shown) that is to be engaged with the distal end of a lever 318 of the lock lever 300. In a case where a lever operation portion 322 of the lever 318 is moved, the engagement between the distal end of the lever 318 and the opening is released. In a case where the push rod 240 is moved in a longitudinal direction, the fiber rod 202 can be removed from the distal end-storage portion 214.

The proximal end-storage portion 220 includes a sliding groove 228 extending in the axial direction of the blood collection instrument 200 and a protrusion 242 of the push rod 240 is inserted into the sliding groove 228, so that the rotation of the push rod 240 about the axial direction is restricted.

In the collection of a blood sample using the blood collection instrument 200, a subject to be examined oneself pricks the distal end portion or the like of a finger with a lancet for collecting blood, and makes the fiber rod 202, which is held by the case 210 of the blood collection instrument 200, come into contact with a blood sample flowing out of the skin. Since the blood sample is absorbed in the pores of the fiber rod 202, the subject to be examined can collect the blood sample in the fiber rod 202. The subject to be examined ends the collection of a blood sample at a point of time when the subject to be examined checks that the entire fiber rod 202 has become red.

(Dilution of Blood Sample)

The cap 424 is removed from the blood collection container 410 of the storage instrument 400. The fiber rod 202, which has absorbed the blood sample by the blood collection instrument 200, is put into the diluent 422 from the upper end opening of the blood collection container 410. The opening formed at the upper end of the blood collection container 410 is sealed with the cap 424.

Figure 6:
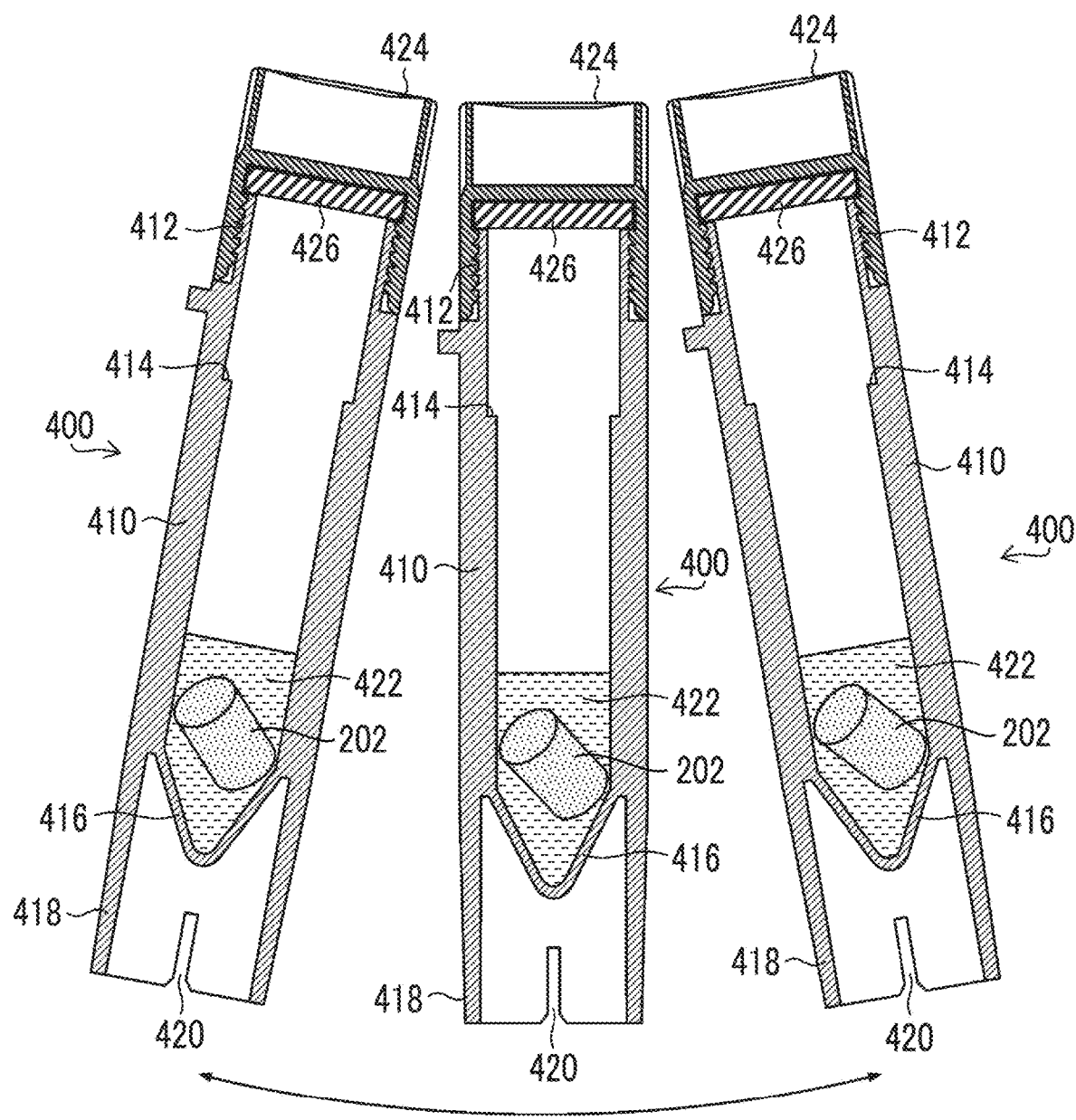
FIG. 6 is a diagram showing an example where a blood sample is released from a fiber rod.

As shown in FIG. 6, the subject holds the upper portion of the blood collection container 410 and shakes the blood collection container 410 dozens of times like a pendulum to release the blood sample to the diluent 422 from the fiber rod 202. Since the blood sample is dissolved into the diluent 422, a dilution of the blood sample is stored in the storage instrument 400.

In a case where the diluent 422 has become red as a whole, the subject finishes shaking the blood collection container 410.

[Separation Instrument]

There is a possibility that the blood sample collected by the blood collection instrument 200 is in a diluted state in the storage instrument 400 for a long time until being analyzed. For example, in a case where the hemolysis of red blood cells occurs during that period, there is a possibility that materials, enzymes, or the like present in the blood cells are eluted into plasma or serum and thus affect the results of the examination or the absorption of eluted hemoglobin affects a case where the amount of analysis target component is measured using optical information, such as the optical absorption of an analysis target component. Accordingly, it is preferable that hemolysis is prevented. For this purpose, a separation instrument used to separate and recover a plasma component from a dilution of the blood sample is included in the self-blood-collecting examination kit. A preferred example of the separation instrument is a separation membrane. For example, in a case where pressure is applied to the dilution of the blood sample, the separation membrane can be used to capture blood cell components and to allow plasma components to pass therethrough to separate blood cells and to recover plasma components. In this case, it is preferable that an anticoagulant is used. Further, to ensure measurement accuracy, it is preferable that plasma having passed through the separation membrane does not flow back to the blood cell side. For this purpose, specifically, a backflow prevention unit disclosed in JP2003-270239A can be provided as a component of the kit.

Figure 7:
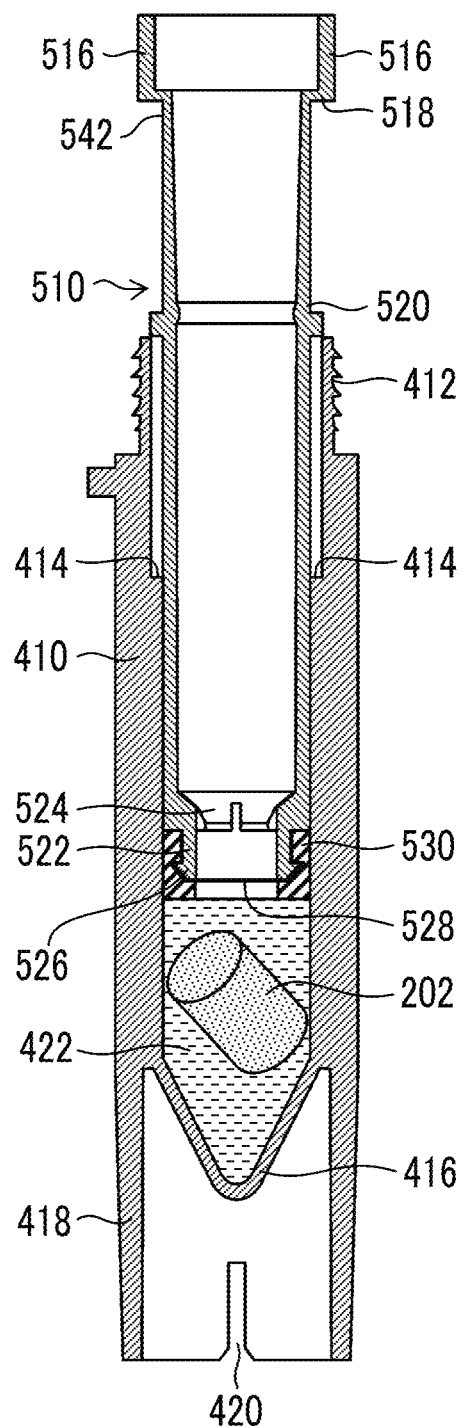
FIG. 7 is a diagram showing that a cylinder is inserted into a blood collection container.

FIG. 7 is a diagram showing that the cylinder 510 is inserted into the blood collection container 410 in which the fiber rod 202 and the dilution of the blood sample are stored.

The cylinder 510 is made of a transparent material and has a cylindrical shape. An increased-diameter portion 516 is formed at an upper end portion 542 of the cylinder 510. The increased-diameter portion 516 is connected to a body portion 520 through a thin wall portion 518. A reduced-diameter portion 522 is formed at a lower end portion of the cylinder 510. A locking protrusion portion 524 is formed on the inner surface of the reduced-diameter portion 522. In addition, an outer flange portion 526 is formed at the lower end portion of the reduced-diameter portion 522. A lower end opening portion of the outer flange portion 526 is covered with a filtration membrane 528 functioning as a separation instrument. The filtration membrane 528 is adapted to allow plasma, which is contained in blood, to pass therethrough and to prevent blood cells from passing therethrough. A cover 530 made of silicone rubber is mounted on the outer periphery of the reduced-diameter portion 522.

In a case where the cylinder 510 is inserted into the blood collection container 410, the filtration membrane 528 held by the cylinder 510 is moved toward the bottom portion 416 of the blood collection container 410. In this case, plasma is moved to the cylinder 510 through the filtration membrane 528 and blood cells remain in the blood collection container 410 without passing through the filtration membrane 528.

Since the outer diameter of the cover 530 is larger than the outer diameter of the body portion 520 of the cylinder 510, the cylinder 510 is moved down in a state where the cylinder 510 is in close contact with the inner surface of the blood collection container 410. Accordingly, there is no concern that the diluent 422 present in the blood collection container 410 leaks to the outside through a gap between the blood collection container 410 and the cylinder 510 in a step of inserting the cylinder 510 into the blood collection container 410.

Figure 8:
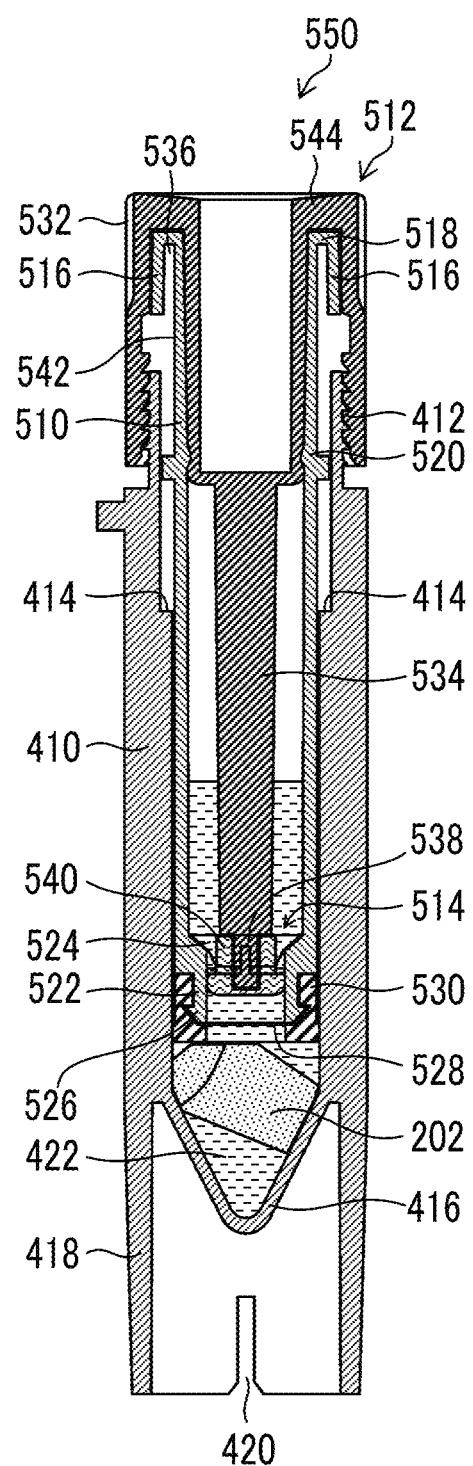
FIG. 8 is a diagram showing that the storage instrument and the cylinder are sealed by a cap.

Next, the storage instrument 400 and the cylinder 510 are sealed with the cap 512 as shown in FIG. 8. The cap 512 can be threadedly engaged the storage instrument 400, and the sealing member 514, which prevents plasma present in the cylinder 510 from flowing back into the blood collection container 410, is provided at the lower end of the cap 512.

The cap 512 includes a substantially cylindrical knob portion 532 and a shaft portion 534 that extends downward so as to be concentric with the knob portion 532. A cylindrical space 536 into which the increased-diameter portion 516 of the cylinder 510 can be fitted is formed inside the upper end portion of the knob portion 532, and threads are formed below the cylindrical space 536 and can be threadedly engaged with a screw. A lower end portion 538 of the shaft portion 534 is formed in the shape of a pin, and the sealing member 514 is attachably and detachably provided at the lower end portion 538. The sealing member 514 is made of silicone rubber. The lower end portion of the sealing member 514 is formed in the shape of an outer flange and has a substantially columnar shape, and a stepped portion 540 is formed over the outer periphery thereof. The knob portion 532 includes a top portion 544.

The knob portion 532 of the cap 512 is threadedly engaged with the threaded portion 412 of the storage instrument 400, so that the storage instrument 400 is sealed. In a case where the knob portion 532 is rotated, the thin wall portion 518 is fractured by torsion. As a result, the cylinder 510 is separated into the body portion 520 and the increased-diameter portion 516. In a case where the knob portion 532 is further rotated, the upper end portion 542 of the body portion 520 enters the space 536 formed inside the increased-diameter portion 516. In a case where the knob portion 532 is threadedly engaged with the threaded portion 412 up to the lowest portion, the sealing member 514 is fitted to the reduced-diameter portion 522. A flow passage between the blood collection container 410 and the cylinder 510 is sealed with the sealing member 514. The sealing member 514 prevents the mixing of plasma and blood cells that is caused by a backflow.

The liquid sample-collecting pipe 550 containing plasma components separated from blood as described above is put in the packaging container 110, and is sent to a medical institution or an examination institution by post. The liquid sample-collecting pipe 550 corresponds to a combination of the storage instrument 400, the cylinder 510, and the cap 512.

First Embodiment

Figure 9:
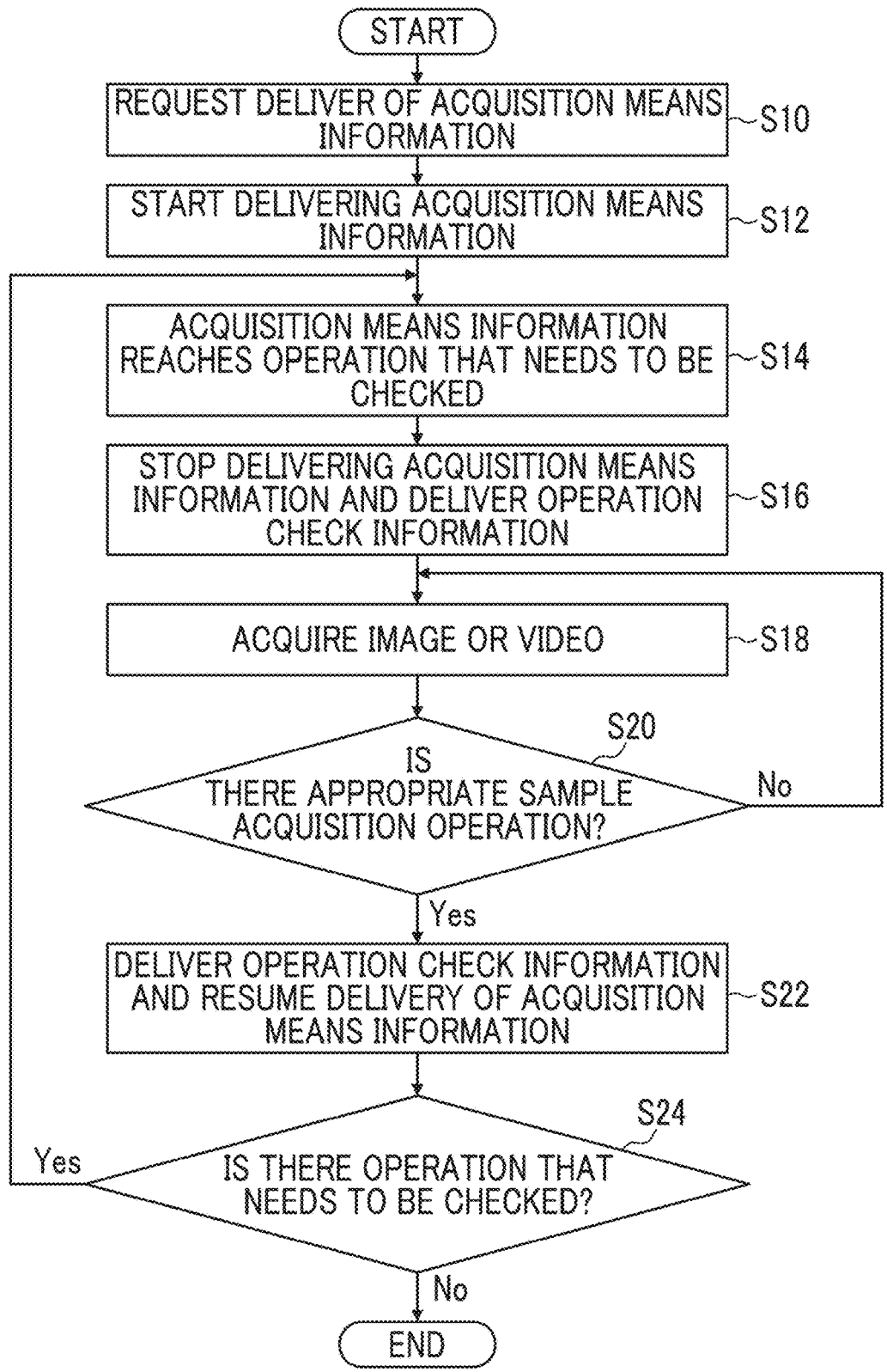
FIG. 9 is a flowchart showing the procedure of a sample acquisition information management method according to a first embodiment.

Next, a sample acquisition information management method using the self-blood-collecting examination kit will be described. FIG. 9 is a flowchart showing the procedure of a sample acquisition information management method according to a first embodiment. In the sample acquisition information management method, first, a subject requests the delivery of acquisition means information (Step S10). A request for the acquisition means information is made in a case where the subject makes an input using the operation unit 28 of the terminal 14.

Next, the output control section 20B starts delivering the acquisition means information through the output unit 18 according to a subject's request (Step S12). The acquisition means information is delivered to the display unit 26 of the terminal 14, and is displayed by the display unit 26. It is preferable that the acquisition means information is a video showing the procedure of a sample acquisition operation. The acquisition means information may be successive images showing the procedure of the sample acquisition operation. The subject can perform the sample acquisition operation while checking the acquisition means information.

In a case where the acquisition means information, which is being delivered, reaches an operation (predetermined sample acquisition operation) where the sample acquisition operation of the subject needs to be checked (Step S14), the output control section 20B stops delivering the acquisition means information and delivers operation check information (Step S16). The operation check information is an image, which is used to request the image or the video of the sample acquisition operation of the subject, and the image of a normal sample acquisition operation serving as a sample. Alternatively, an image serving as the sample of a failure example can also be displayed.

FIGS. 10 to 13 are diagrams showing examples the operation check information to be delivered in Step S16. Examples of the operation where the sample acquisition operation of the subject needs to be checked can include a state where the subject has made the fiber rod absorb blood (FIG. 10), a state where the subject drops the fiber rod into the storage instrument and shakes the storage instrument (FIG. 11), a state where the subject makes the separation instrument provided at the distal end of the cylinder reach the bottom of the storage instrument (FIG. 12), a state where the subject inserts the sealing member provided at the cap into the cylinder, and the like.

Figure 10:
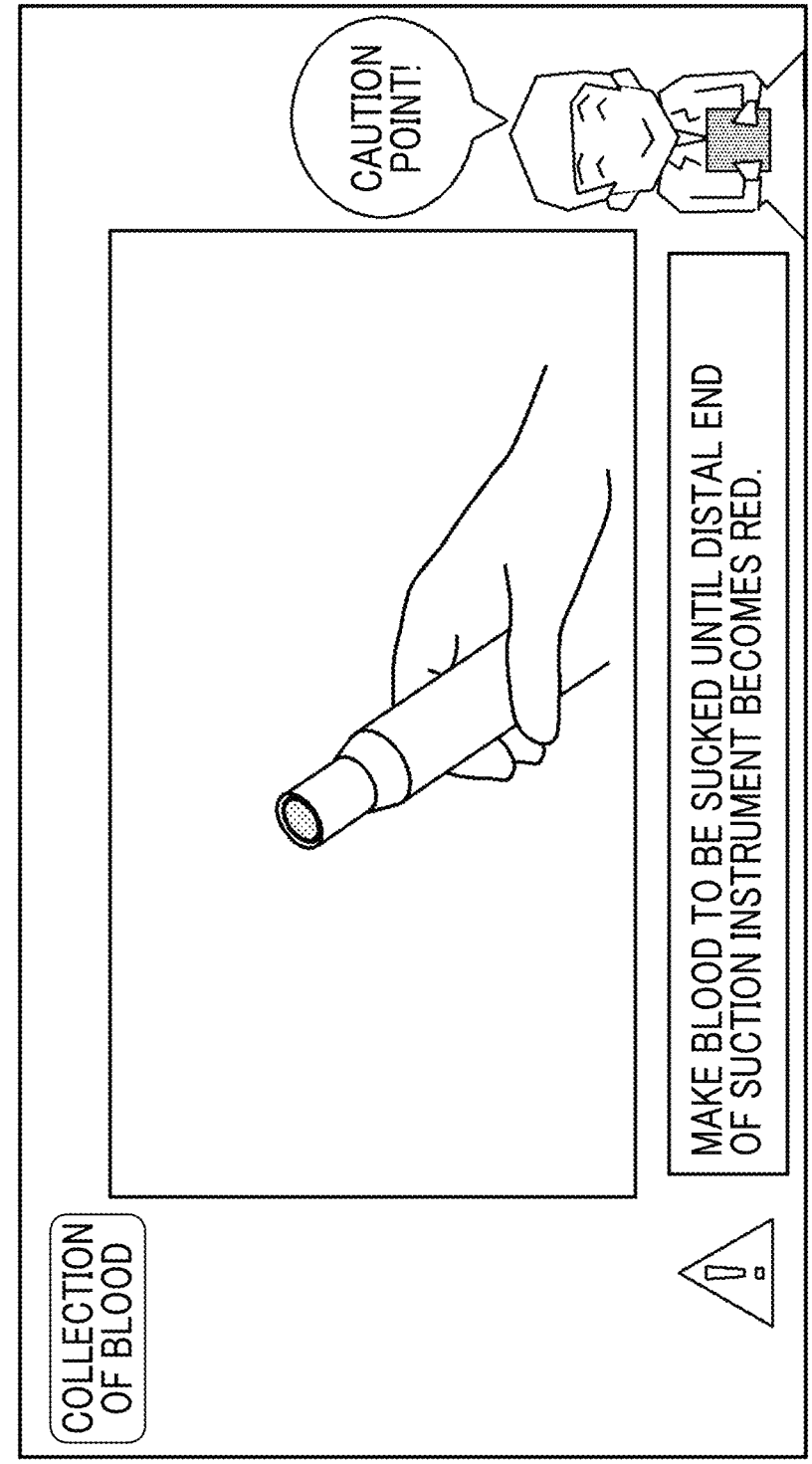
FIG. 10 is a diagram showing an example of operation check information.
Figure 11:
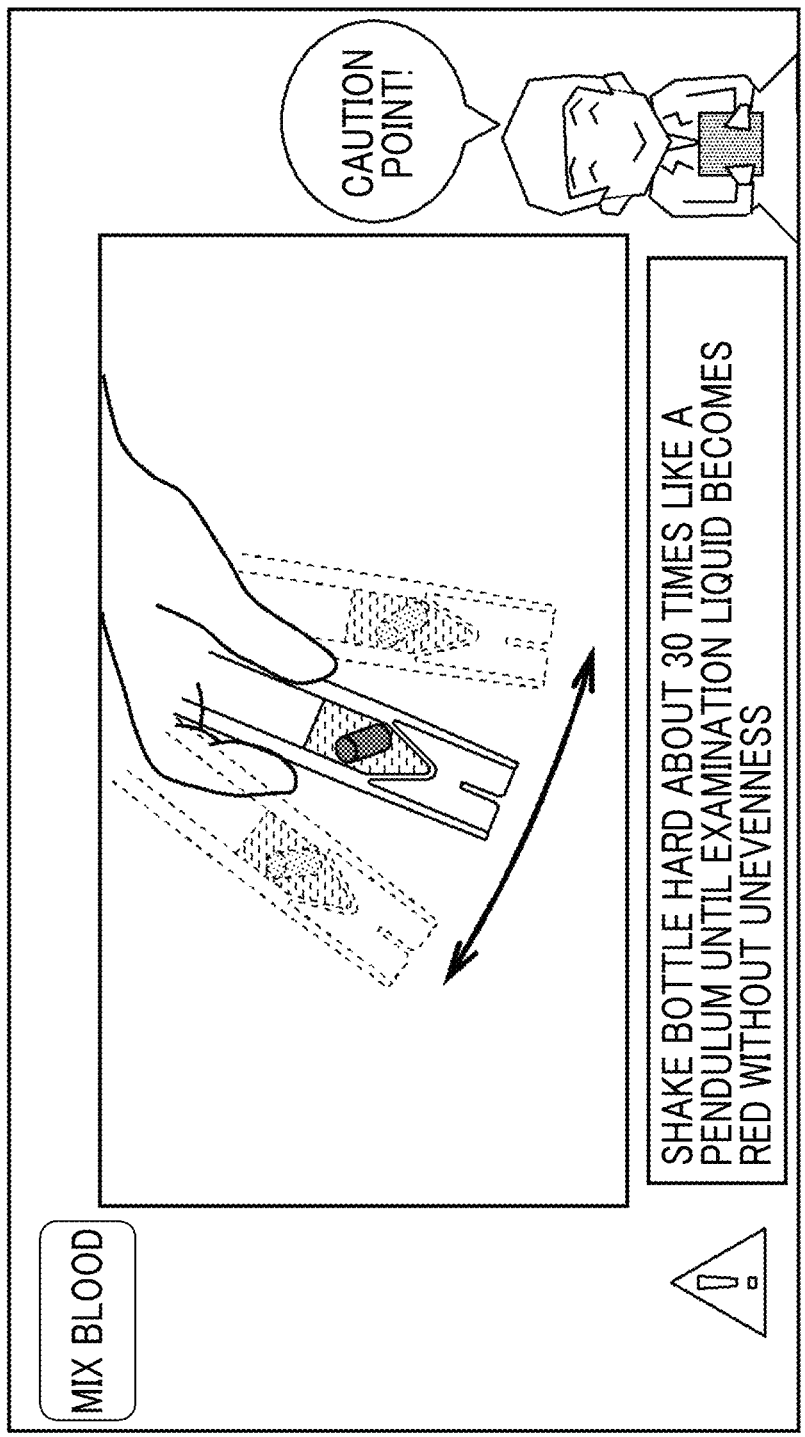
FIG. 11 is a diagram showing another example of operation check information.

The subject can collect the amount of blood sufficient for analysis by making the fiber rod absorb blood until the fiber rod becomes red as shown in FIG. 10 as the operation that needs to be checked. The subject makes the blood, which is absorbed in the fiber rod, be released to the diluent by shaking the storage instrument like a pendulum as shown in FIG. 11 after putting the fiber rod into the storage instrument. In a case where the subject shakes the storage instrument in a vertical direction at this time, there is a case where the hemolysis of red blood cells occurs and affects the results of the examination. In a case where the subject shakes the storage instrument like a pendulum as shown in FIG. 11, hemolysis can be prevented.

Figure 12:
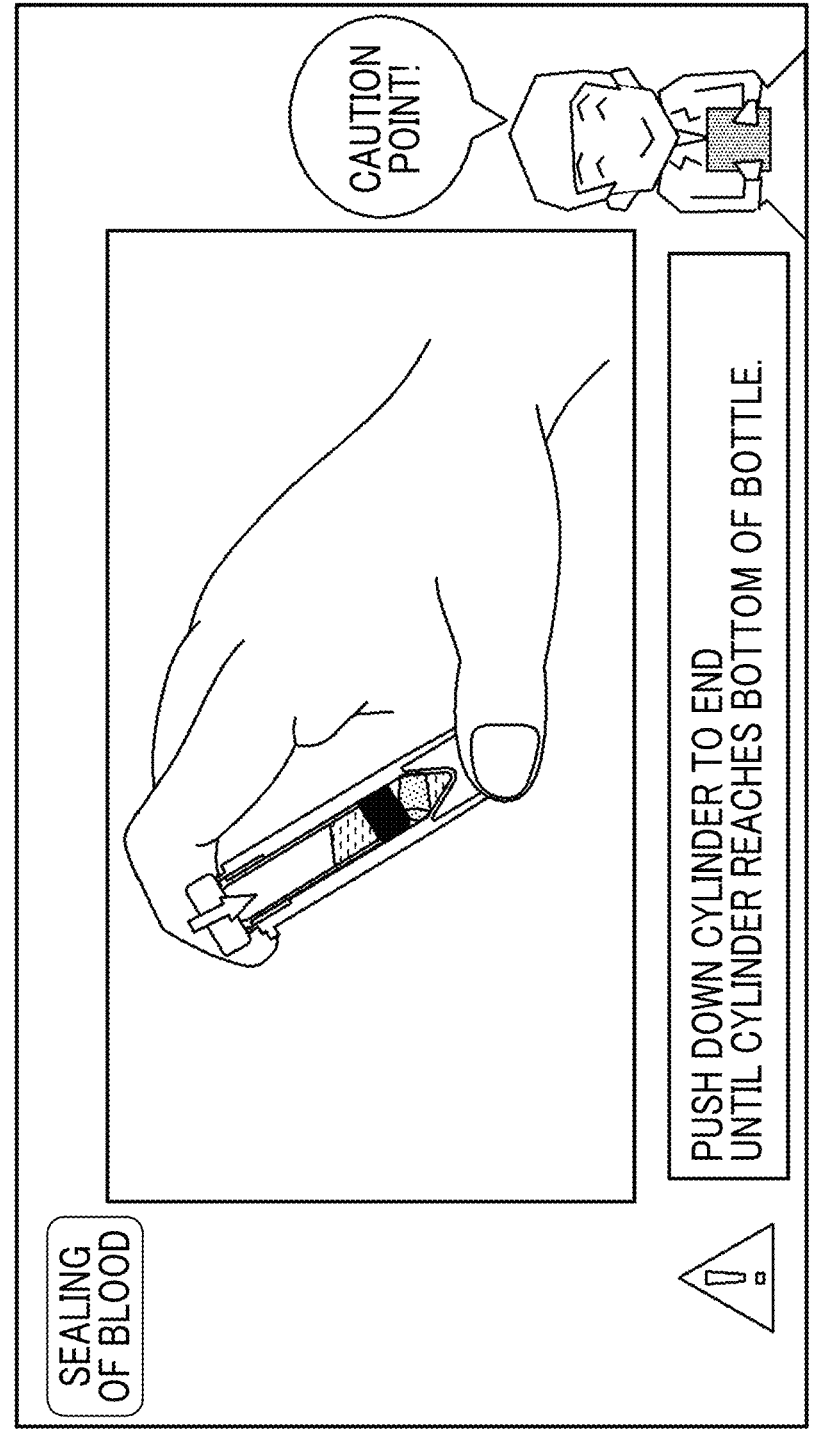
FIG. 12 is a diagram showing still another example of operation check information.
Figure 13:
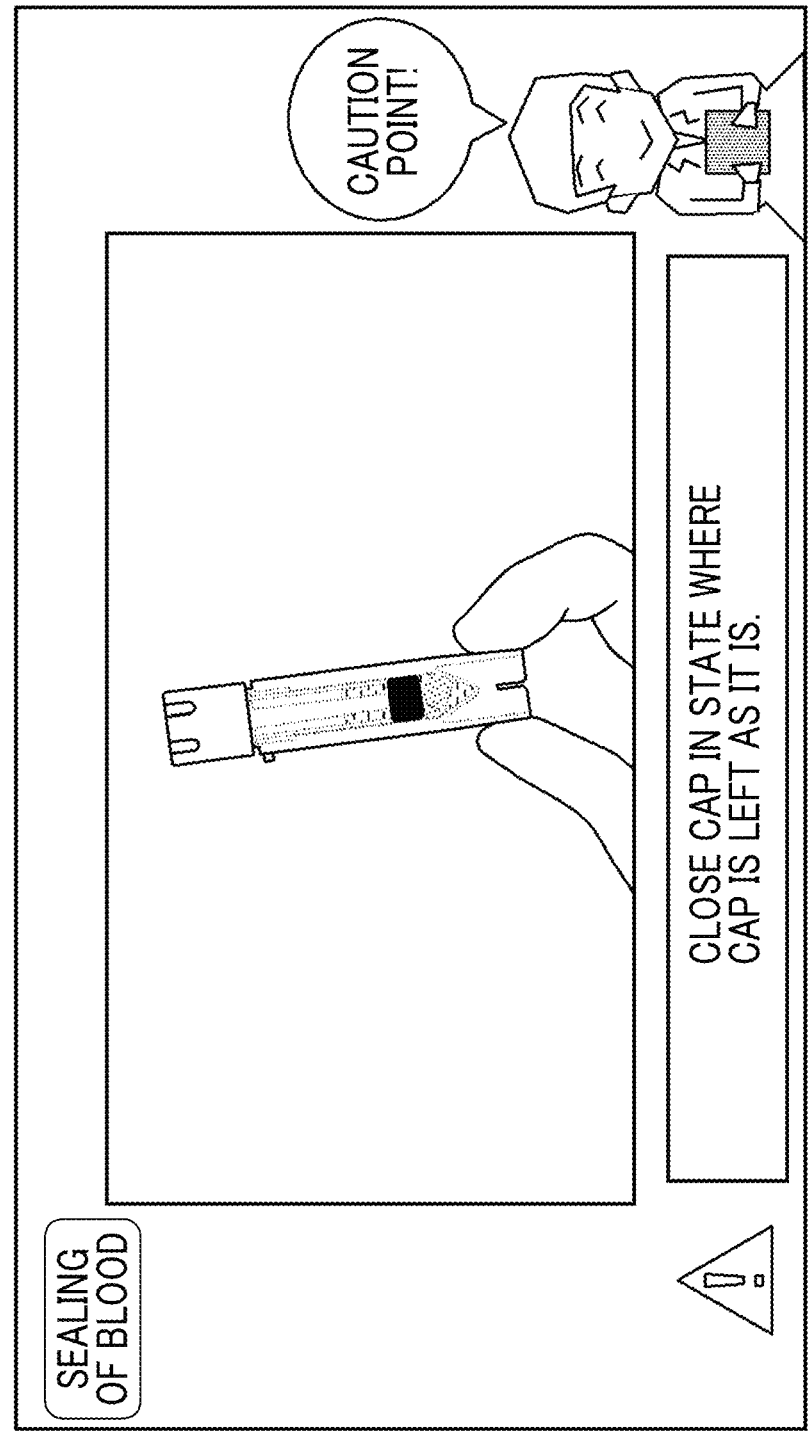
FIG. 13 is a diagram showing yet another example of operation check information.

Further, since the subject can make plasma, which is separated using the filtration membrane, be moved into the cylinder by making the cylinder reach the bottom of the storage instrument (bottle) as shown in FIG. 12, the subject can collect plasma required for analysis. In a case where the subject closes the cap as shown in FIG. 13, the sealing member provided at the lower end of the cap seals the flow passage between the blood collection container and the cylinder. Accordingly, since the plasma present in the cylinder can be prevented from flowing back into the blood collection container, only the plasma can be reliably separated and stored. As a result, hemolysis can be prevented. The subject can collect the sufficient amount of component used for analysis by checking the above-mentioned operations as the predetermined sample acquisition operation that needs to be checked.

As shown in FIGS. 10 to 13, the images of the normal operations as the sample acquisition operations are displayed as the operation check information. The subject who receives a request for the image or the video of the sample acquisition operation takes an image or a video by the imaging unit 24 of the terminal 14 in Step S16, and transmits the taken image or video to the server device 12 (Step S18). The image acquisition unit 16 of the server device 12 acquires the image or the video transmitted from the terminal 14. An image serving as the sample of a failure example may be displayed as the operation check information. The subject can transmit the image of the normal operation by one time of imaging.

The determination section 20A of the processing unit 20 determines whether or not the image or the video acquired by the image acquisition unit 16 is normal as the sample acquisition operation (Step S20). The determination of whether or not the acquired image is normal is made by the check of whether or not the acquired image is the image of a normal sample acquisition operation stored in the information storage section 22B.

For example, in the case shown in FIG. 10 where the subject makes the fiber rod absorb blood, whether or not the acquired image is normal can be determined from the color of the fiber rod. Since the entire fiber rod is white before the fiber rod absorbs blood, it can be determined that an operation is a normal operation in a case where the entire fiber rod has become red. With regard to a method shown in FIG. 11 of shaking the storage instrument, the blood is released and the diluent becomes red as the subject shakes the storage instrument. Whether or not the acquired image is normal can be determined from the number of times of the translation of the diluent, which has become red, in a lateral direction. In the case shown in FIG. 12 where the subject makes the cylinder reach the bottom of the bottle, whether or not the acquired image is normal can be determined from a positional relationship between the distal end (filtration membrane) of the cylinder and the bottle. Further, with regard to the insertion of the sealing member shown in FIG. 13, whether or not the acquired image is normal can be determined from a positional relationship between the distal end (filtration membrane) of the cylinder and the cap. The subject takes an image where blood is sucked with a pipette in a case where the subject sucks blood with a pipette or the like as another example of an image where blood is collected. In a case where it can be checked that the amount of sucked blood corresponds to the position of a target gradation, it can also be determine that the acquired image is a normal operation image.

Returning to FIG. 9, in a case where it is determined in Step S20 that the sample acquisition operation is normal, the output control section 20B releases the stop of the delivery of the acquisition means information and resumes the delivery of the acquisition means information. The acquisition means information is delivered through the output unit 18, so that the display of the acquisition means information on the display unit 26 of the terminal 14 is resumed. The subject can continue to perform the sample acquisition operation on the basis of the acquisition means information of which the display is resumed.

In a case where it is determined in Step S20 that the sample acquisition operation is abnormal, processing returns to Step S18 and the subject repeats the sample acquisition operation so that it is determined that the requested sample acquisition operation is a normal operation. In a case where processing returns to Step S18, the output control section 20B may perform control to deliver the image of a normal sample acquisition operation again. Further, the output control section 20B can make advice, which allows the requested sample acquisition operation to be determined as a normal sample acquisition operation, be displayed. For example, in a case where the amount of blood absorbed in the fiber rod is insufficient (a white region remains in the fiber rod or the color of the fiber rod is light), the output control section 20B may make "please let the fiber rod suck blood" or the like be displayed.

After the output control section 20B resumes the delivery of the acquisition means information in Step S22, the subject resumes the sample acquisition operation. In a case where there is an operation where the sample acquisition operation of the subject needs to be checked among remaining sample acquisition operations (step S24), processing returns to Step S14. In a case where the acquisition means information, which is being delivered, reaches an operation that needs to be checked, the output control section 20B stops delivering the acquisition means information and delivers the operation check information (Step S16). Hereinafter, taking an image or a video (Step S18), the determination of the sample acquisition operation (Step S20), and the resumption of the delivery of the acquisition means information (Step S22) are performed likewise, and the sample acquisition operation is checked.

In a case where there is no sample acquisition operation to be checked (Step S24), the subjects ends the sample acquisition operation according to the acquisition means information.

Figure 14:
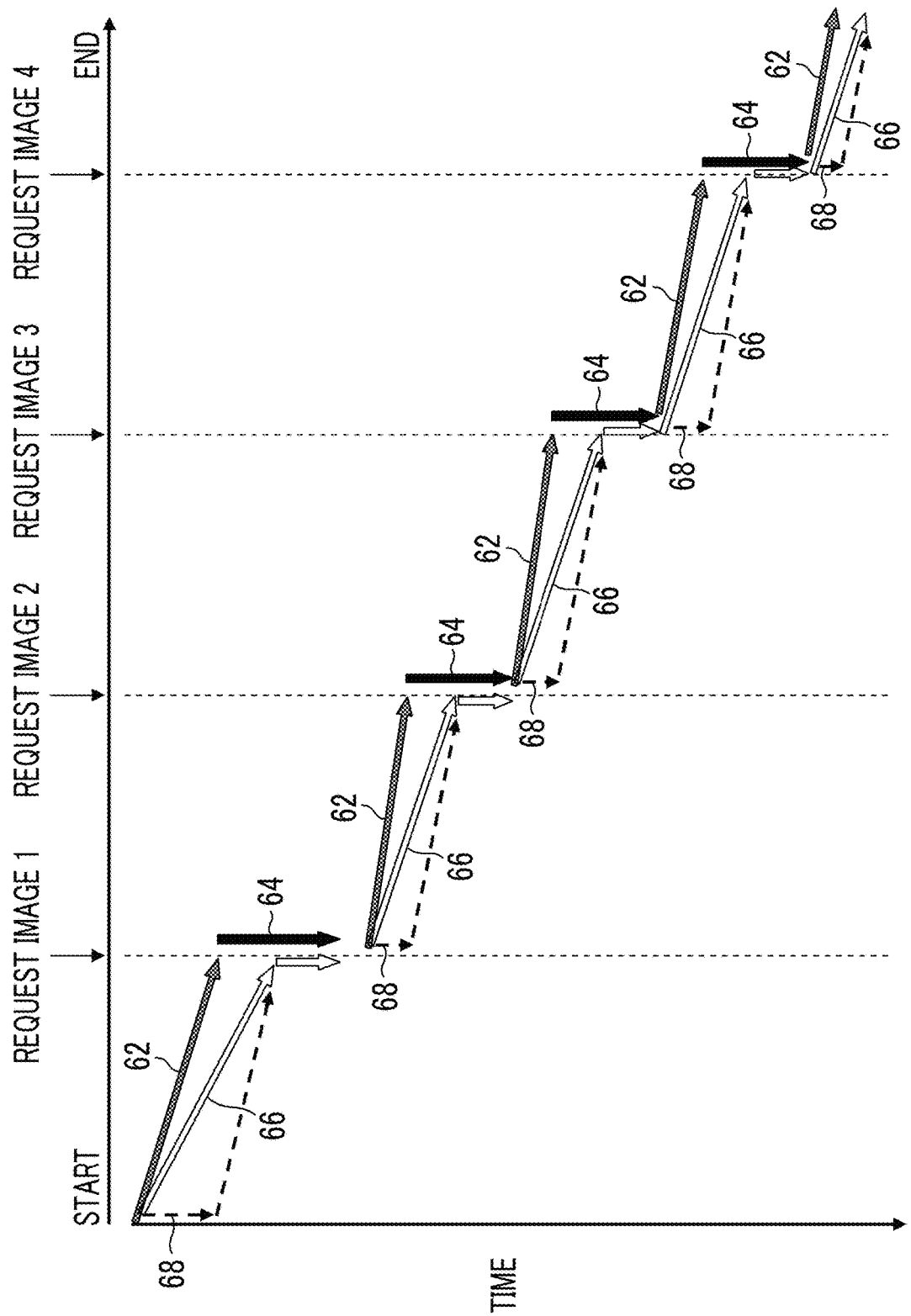
FIG. 14 is a diagram showing a relationship between the delivery of acquisition means information and a sample acquisition operation of a subject.

FIG. 14 is a diagram showing a relationship between the delivery of acquisition means information and the sample acquisition operation of the subject. In FIG. 14, a vertical axis represents time and a horizontal axis represents the step of the sample acquisition operation. Further, an arrow 62 indicates the delivery of the acquisition means information, an arrow 64 indicates the delivery of the operation check information, an outlined arrow 66 indicates a subject A, and a dotted-line arrow 68 indicates a subject B.

As shown in FIG. 14, the delivery of the acquisition means information is started in a case where a sample acquisition operation based on the sample acquisition information management method is started. The subject A performs the sample acquisition operation according to the delivered acquisition means information.

In a case where the delivery of the acquisition means information reaches a request image 1 in the sample acquisition operation (Step S14 in FIG. 9), the output control section 20B stops delivering the acquisition means information and delivers the operation check information. The subject A takes the image of one's own sample acquisition operation on the basis of the request image 1, and transmits the taken image to the image acquisition unit 16 of the server device 12. The image acquired by the image acquisition unit 16 is determined by the determination section 20A, and the delivery of the acquisition means information is resumed after it is checked that the acquired image is the image of a normal operation. The subject A performs the sample acquisition operation on the basis of the acquisition means information again. In FIG. 14, there are four times of an operation that needs to be checked (request images 1 to 4), and the output control section 20B stops delivering the acquisition means information and delivers the operation check information at each time. Then, the operation is checked using the image, and the acquisition means information is not delivered until it is checked that the operation is a normal operation. Accordingly, whether the acquired image is a normal image (an appropriate operation) can be checked for each of the operations that are requested by the respective request images. Since all operations are not managed as the sample acquisition operation and an image is checked for each predetermined sample acquisition operation as described above, the sample acquisition operation can be reliably performed. Further, since the delivery of the acquisition means information is stopped in the case of a predetermined sample acquisition operation, it is possible to prevent the sample acquisition operation, which is being performed by the subject, and the sample acquisition operation of the acquisition means information, which is being delivered, from being extremely different from each other.

As in the case of the subject A shown in FIG. 14, a subject may perform the sample acquisition operation while looking at the delivered acquisition means information. Further, as in the case of the subject B shown in FIG. 14 by the dotted-line arrow 68, a subject may perform the sample acquisition operation after looking at the acquisition means information, which is delivered, until the operation check information is delivered. A subject who acquires a sample for the first time or has less experience in the acquisition of a sample can acquire a sample as with the subject B.

Figure 15:
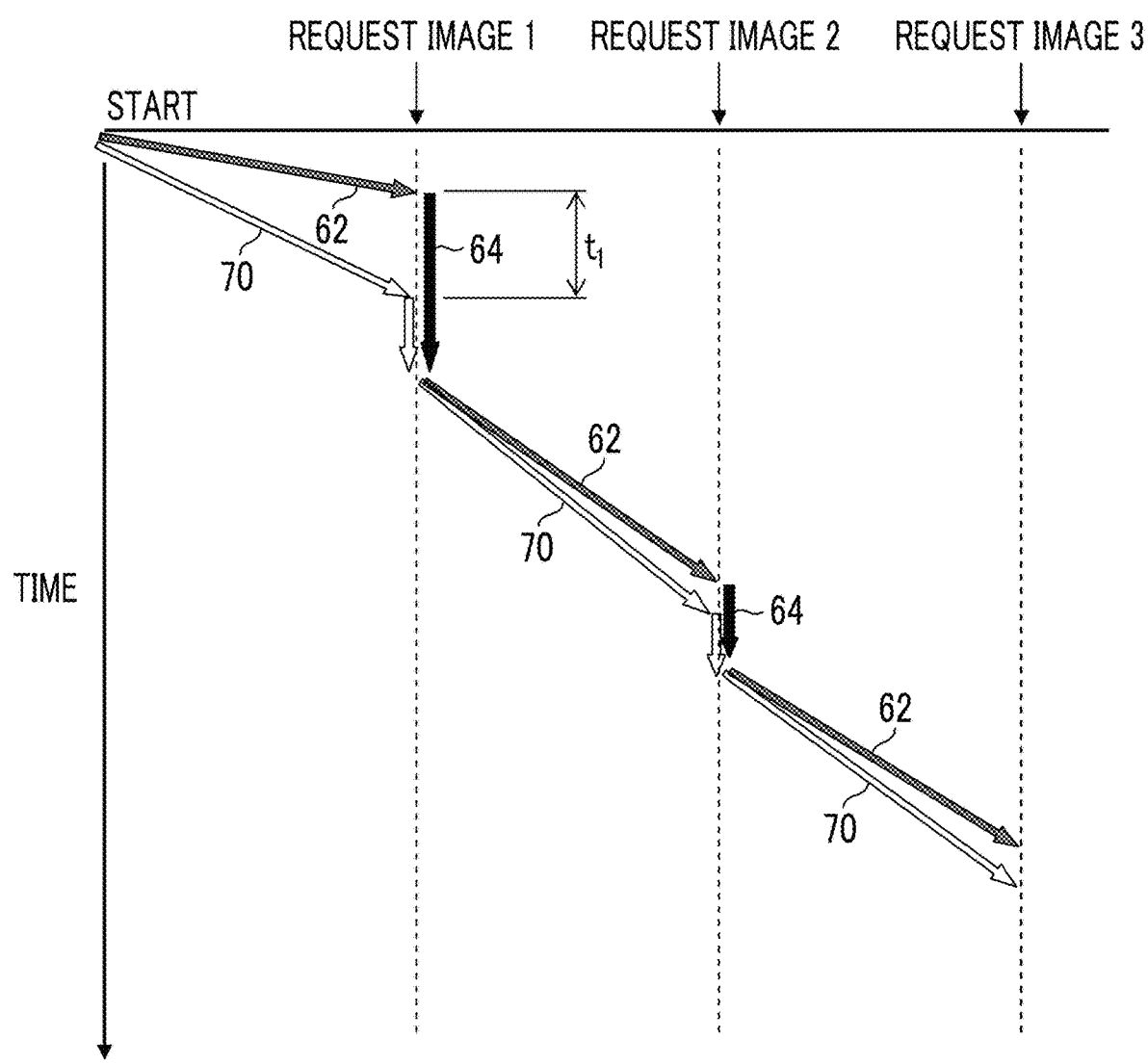
FIG. 15 is another diagram showing a relationship between the delivery of acquisition means information and a sample acquisition operation of a subject.

FIG. 15 is another diagram showing a relationship between the delivery of acquisition means information and sample acquisition operation of a subject. An arrow 62 shown in FIG. 15 indicates the delivery of the acquisition means information, an arrow 64 indicates the delivery of the operation check information, and an outlined arrow 70 indicates a subject C. The delivery of the acquisition means information up to a request image 1 and the delivery of the operation check information are performed in the same method as the method shown in FIG. 14. The subject C performs a sample acquisition operation on the basis of the acquisition means information. Further, the subject transmits the image taken by the imaging unit 24 of the terminal 14 to the server device 12 in a case where the subject checks the operation (in a case where the request image 1 is requested). At this time, in a case where the determination section 20A determines that a time $\mu l$ having passed until the subject C transmits the image from the start of the delivery of the operation check information is long, the output control section 20B may perform control to reduce the delivery speed of the acquisition means information. Subsequent acquisition means information can be delivered in consideration of a time having passed until a first operation (the operation of the request image 1), which needs to be checked, from the start of a sample acquisition operation. For example, in FIG. 15, the delivery of the acquisition means information up to a request image 2 from the request image 1 and the delivery speed of the acquisition means information up to a request image 3 from the request image 2 are reduced, and subsequent acquisition means information can be delivered according to a time having passed until an image is delivered with the request image 1 from the start of the sample acquisition operation of the subject. In a case where the time $\mu l$ having passed until the transmission of the taken image from the stop of the delivery of the acquisition means information is long in the check of the first sample acquisition operation (the request image 1), the determination section 20A determines that the sample acquisition operation of the subject C does not follow the delivery of the acquisition means information. The output control section 20B changes the delivery speed of the acquisition means information to be output through the output unit 18 according to the time of the sample acquisition operation having passed until the check of the first sample acquisition operation (the request image 1), so that the acquisition means information can be delivered according to the sample acquisition operation of the subject C. Accordingly, the subject C can perform the sample acquisition operation with a margin of time on the basis of the acquisition means information.

The acquisition means information is delivered in the sample acquisition information management method. However, in the case of a person or the like who has much experience in the use of a self-blood-collecting examination kit, only the operation check information can be delivered without the delivery of the acquisition means information. Since a subject can perform a sample acquisition operation up to a predetermined sample acquisition operation at one's own pace in a case where only the operation check information is delivered, the subject can check only an important operation.

Second Embodiment

Figure 16:
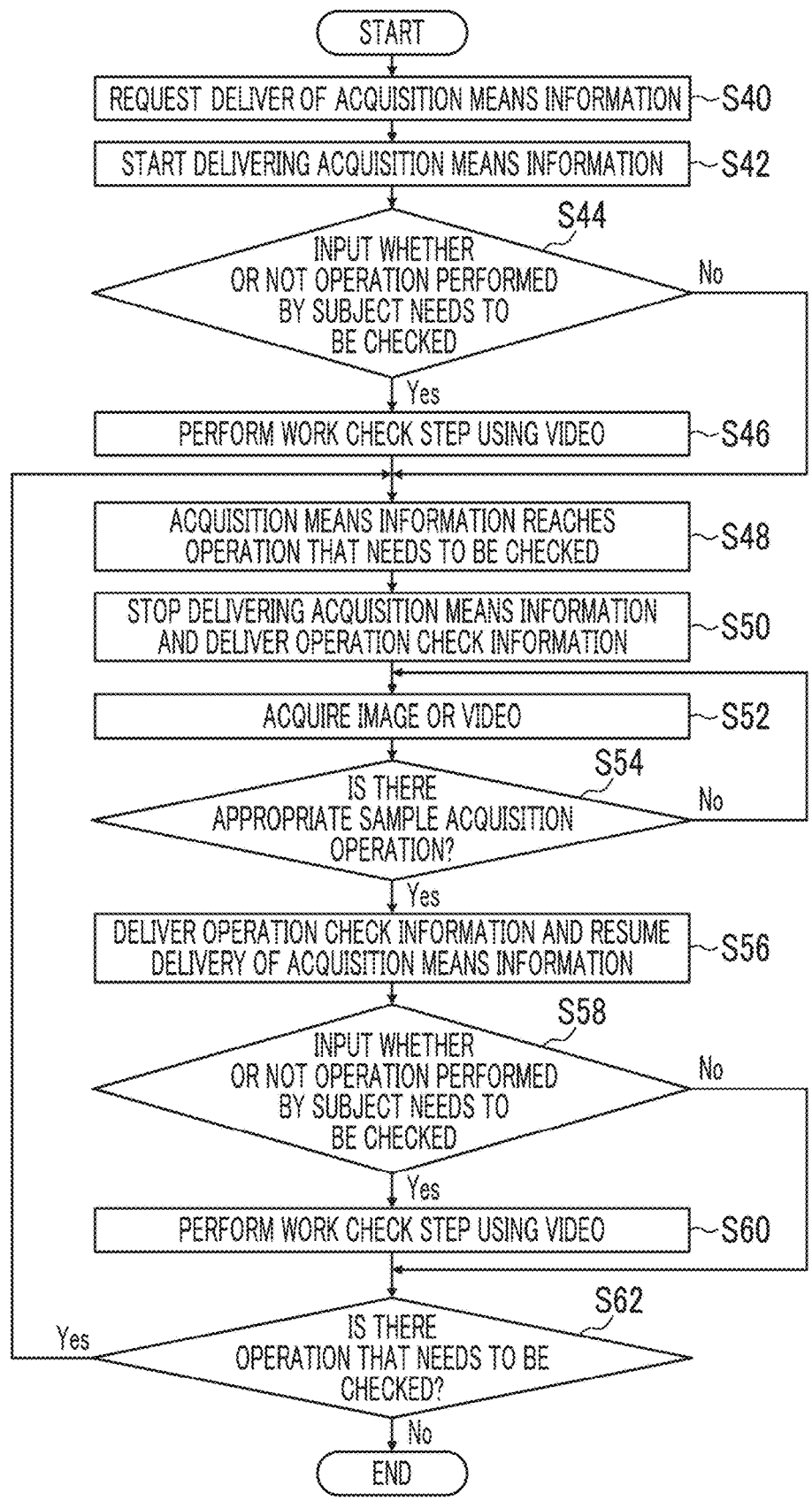
FIG. 16 is a flowchart showing the procedure of a sample acquisition information management method according to a second embodiment.

FIG. 16 is a flowchart showing the procedure of a sample acquisition information management method according to a second embodiment. The sample acquisition information management method according to the second embodiment is different from the sample acquisition information management method according to the first embodiment in that the video of a sample acquisition operation of a subject is taken and the sample acquisition operation of the subject is checked using this video as well.

Steps S40 and S42 are performed in the same manner as the Steps S10 and S12 of the first embodiment. Next, the subject inputs whether or not the operation needs to be checked (Step S44). The input is made through the operation unit 28 of the terminal 14.

In a case where the subject desires to check the operation, a work check step using a video is performed (Step S46). FIG. 17 is a flowchart of the work check step using a video. In a case where the subject desires to check the operation, acquisition means information is displayed on the terminal 14 and the subject starts taking the video of subject's own sample acquisition operation from the imaging unit 24 of the terminal 14 (Step S100). At this time, the subject's own sample acquisition operation taken by an in-line camera provided in the imaging unit 24 may be displayed on the display unit 26. The video taken by the imaging unit 24 is acquired by the image acquisition unit 16.

The determination section 20A sequentially determines whether or not the video taken in Step S100 corresponds to an appropriate operation (normal operation) (Step S102). In a case where the imaged sample acquisition operation is performed as a normal operation, the video continues to be taken and an operation check step ends.

In a case where there is an inappropriate operation in Step S102, the determination section 20A determines whether or not the operation can be redone (Step S104). In a case where the operation can be redone, the output control section 20B outputs warning information through the output unit 18 (Step S106). In a case where the warning information is output, the display unit 26 of the terminal 14 may display that the operation is incorrect or a warning may be given by sound. In a case where the warning is issued, the subject can recognize that work currently being performed is not appropriate, can interrupt the work, and can redo the work with an appropriate action. A normal (appropriate) work image may be displayed as the warning information.

Examples of an operation where the warning information is output include a case where a position pricked with the lancet is not the distal end portion of a finger, a case where the subject is to drop the fiber rod having absorbed blood into a portion other than the storage instrument, a case where the subject is to close the cap without inserting the cylinder into the storage instrument, a case where a cold insulation material is not set in a post container, and the like.

Further, in a case where it is determined in Step S104 that the operation cannot be redone, the video is stored in the storage unit (Step S108). Furthermore, the determination section 20A transmits to the output control section 20B that an operation (action), which cannot be redone and from which a normal image cannot be acquired, has been performed. In the output control section 20B, in a display for requesting the sample acquisition operation of the subject, it is possible to prevent the subject from being not able to recognize that a sample acquisition operation is appropriate and to prevent the delivery of the acquisition means information from being not resumed.

Examples of the action that is determined to be impossible to be redone in Step S104 include a case where the diluent present in the storage instrument is spilled and a case where an unused lancet is not recovered. An accurate analysis cannot be made in a case where the diluent is spilled. Further, since the sample examination kit needs to be treated as medical waste, the sample examination kit can be checked later in a case where a video is stored even though an unused lancet does not need to be recovered.

Taking a video ends in a case where the acquisition means information corresponds to an operation that needs to be checked, and the work check step (Step S46) ends. Further, in a case where the subject does not desire to check an operation, the acquisition means information is delivered and is displayed on the display unit 26. Then, as in the first embodiment, in a case where the acquisition means information reaches an operation where the sample acquisition operation of the subject needs to be checked (Step S48), the output control section 20B stops delivering the acquisition means information and delivers the operation check information (Step S50). Steps S52 to S56 can be performed by Steps S18 to S22 of the first embodiment and applied operations.

In a case where the delivery of the acquisition means information is resumed, the subject inputs whether or not the sample acquisition operation needs to be checked (Step S58). In a case where the subject desires to check the operation, a work check step (Step S60) is performed. The work check step of Step S60 can also be performed in the same manner as Step S46. In a case where there is an operation that needs to be checked (Step S62) after the work check step (Step S60) ends, processing returns to Step S48 and the same procedure is repeated. In a case where there is no operation that needs to be checked (Step S62), the subject performs sample acquisition work according to the delivered acquisition means information and ends the sample acquisition operation.

Further, in the second embodiment, in a case where the determination section 20A determines that a difference in time between the acquired video (subject's action) and the operation of the acquisition means information, which is being delivery, is large in the middle of the taking of a video in the work check steps (Steps S46 and S60), the output control section 20B may stop delivering the acquisition means information until the sample acquisition operation of the subject follows the current acquisition means information. Accordingly, since the subject can prevent the acquisition means information from extremely going ahead of the sample acquisition operation of the subject, the subject can reliably perform the sample acquisition operation.

According to the sample acquisition information management method of the second embodiment, the subject can take the video of an operation or the like that is unstable as the sample acquisition operation, and can progress work while determining the taken video with the determination section 20A. Further, since a warning is given in a case where an operation is not appropriate as the sample acquisition operation, the subject can correct the operation during work. Accordingly, the subject can reliably perform the sample acquisition operation.

In the sample acquisition information management methods according to the first and second embodiments, it is preferable that the image and the video acquired by the image acquisition unit 16 and the unique kit ID provided for a sample examination kit are stored in the image storage section 22A in association with each other. Since the kit ID is associated with the image and the video, the subject can check an image that is determined to be normal during each sample acquisition operation that needs to be checked. For example, in a case where an analyzer checks the sample acquisition operation even though the determination section 20A determines that an operation is a normal operation, the analyzer can easily search for an image or a video later. Further, in a case where the image of a failure example determined to be abnormal is stored in association with a kit ID, the image of one's own failure example is delivered as the operation check information at the time of the acquisition of the next and subsequent samples, so that the subject carefully performs the sample acquisition operation. Accordingly, the subject can smoothly perform the sample acquisition operation.

Furthermore, even in a case where an operation is difficult to be determined as a normal sample acquisition operation in the subsequent work during a sample acquisition operation, the video of the operation is stored in association with a kit ID. Accordingly, in a case where an analyzer certainly knows that there is a mistake in the delivered sample acquisition operation, the analyzer can check what happened by checking the video that is associated with a sample kit.

According to the invention, a subject acquires an image or a video during a predetermined sample acquisition operation and can acquire a sample while determining whether or not the sample acquisition operation is normal using this image or this video. Accordingly, since the subject can reliably perform each step of a sample acquisition operation, the subject can reliably acquire a sample. Therefore, even in a case where the subject collects a sample by oneself, it is possible to make an analysis using the sample.

EXPLANATION OF REFERENCES

10: sample acquisition information management system
12: server device
14: terminal
16: image acquisition unit
18: output unit
20: processing unit
20A: determination section
20B: output control section
22: storage unit
22A: image storage section
22B: information storage section
24: imaging unit
26: display unit
28: operation unit
50: network
62, 64, 66, 68, 70: arrow
100: lancet
110: packaging container
200: blood collection instrument
202: fiber rod
210: case
212: opening
214: distal end-storage portion
216: middle portion
218: flange portion
220: proximal end-storage portion
222: opening
228: sliding groove
240: push rod
242: protrusion
300: lock lever
318: lever
322: operation unit
400: storage instrument
410: blood collection container
412: threaded portion
414: locking portion
416: bottom portion
418: leg portion
420: slit groove
422: diluent
424: cap
426: packing
510: cylinder
512: cap
514: sealing member
516: increased-diameter portion
518: thin wall portion
520: body portion
522: reduced-diameter portion
524: locking protrusion portion
526: outer flange portion
528: filtration membrane
530: cover
532: knob portion
534: shaft portion
536: space
538: lower end portion
540: stepped portion
542: upper end portion
544: top portion
550: liquid sample-collecting pipe
600: self-blood-collecting examination kit
602: case

What is claimed is:

1. A sample acquisition information management device comprising:
an input-output interface configured to acquire at least one of an image or a video of a sample acquisition operation from a user terminal of a subject using a sample examination kit, and output acquisition means information and operation check information to the user terminal; and
at least one processor configured to determine whether or not the image or the video acquired by the input-output interface corresponds to a correct sample acquisition operation, and control display of the acquisition means information and the operation check information,
wherein the at least one processor is further configured to:
control the input-output interface to deliver the acquisition means information to the user terminal according to a request from the user terminal of the subject, stop delivering the acquisition means information in a case where delivery of a predetermined sample acquisition operation of the acquisition means information ends, and deliver the operation check information; and
determine whether or not the image or the video acquired by the input-output interface from the user terminal corresponds to a normal sample acquisition operation, wherein
during the sample acquisition operation,
in a case where it is determined that the sample acquisition operation is normal, the at least one processor is further configured to release the stop of the delivery of the acquisition means information and resume the delivery of the acquisition means information,
in a case where it is determined that the sample acquisition operation is abnormal, the at least one processor is further configured to deliver the operation check information again,
the at least one processor is further configured to measure a time having passed from a start of the delivery of the operation check information until acquisition of the image or the video, and adjust a delivery speed of the acquisition means information according to a length of the time,
in a case where the at least one processor receives an operation to stop the delivery of the operation check information from the user terminal, or in a case where the at least one processor cannot receive the image or the video within a predetermined time, the delivery speed of the operation check information is reduced, and
in a case where the at least one processor further receives the operation to stop the delivery of the operation check information, or in a case where the at least one processor cannot receive the image or the video, the delivery speed of the operation check information is further reduced.

2. The sample acquisition information management device according to claim 1,
wherein the operation check information is a request image for the sample acquisition operation and an image of a normal sample acquisition operation.

3. The sample acquisition information management device according to claim 1, further comprising:
an image storage medium configured to store the image or the video acquired by the input-output interface.

4. The sample acquisition information management device according to claim 3,
wherein the sample examination kit has a unique kit ID for each sample examination kit, and
the image storage medium stores the image or the video acquired by the input-output interface and the kit ID so that the image or the video and the kit ID are associated with each other.

5. The sample acquisition information management device according to claim 1,
wherein the at least one processor is further configured to output warning information via the input-output interface in a case where it is determined that the video acquired by the input-output interface corresponds to an abnormal operation of the subject.

6. The sample acquisition information management device according to claim 1,
wherein the sample examination kit is a self-blood-collecting examination kit, and
the sample examination kit includes a lancet that is used to puncture a skin, a blood collection instrument that includes a fiber rod, a storage instrument that contains a diluent therein, a cylinder that includes a separation instrument for separating plasma and a blood cell, and a cap that includes a sealing member.

7. The sample acquisition information management device according to claim 6,
wherein the sample acquisition operation includes at least one of a state where the fiber rod has absorbed blood, a state where the fiber rod is dropped into the storage instrument and the storage instrument is shaken, a state where the separation instrument provided at a distal end of the cylinder reaches a bottom of the storage instrument, and a state where the sealing member provided at the cap is inserted.

8. The sample acquisition information management device according to claim 6,
wherein the at least one processor is further configured to output warning information via the input-output interface in a case where it is determined that that the video acquired by the input-output interface corresponds to an abnormal operation of the subject, and
the warning information is output in at least one of a case where a position pricked with the lancet is not a distal end portion of a finger, a case where the subject is to drop the fiber rod having absorbed blood into a portion other than the storage instrument, a case where the subject is to close the cap without inserting the cylinder into the storage instrument, and a case where a cold insulation material is not set in a post container.

9. The sample acquisition information management device according to claim 6, further comprising
an image storage medium configured to store the image or the video acquired by the input-output interface,
wherein the sample examination kit has a unique kit ID for each sample examination kit, and
the image storage medium stores the video and the kit ID so that the video and the kit ID are associated with each other, in a case where it is determined that the video acquired by the input-output interface corresponds to at least one of a case where the diluent present in the storage instrument is spilled and a case where the lancet is not recovered when unused.

10. A sample acquisition information management system comprising:
a server configured to be connectable to a terminal through a network,
wherein the server includes:
an input-output interface configured to acquire at least one of an image or a video of a sample acquisition operation from a user terminal of a subject using a sample examination kit, and output acquisition means information and operation check information to the user terminal; and
at least one processor configured to determine whether or not the image or the video acquired by the input-output interface corresponds to a correct sample acquisition operation and control display of the acquisition means information and the operation check information, wherein
the at least one processor is further configured to:
control the input-output interface to deliver the acquisition means information to the user terminal according to a request from the user terminal of the subject, stop delivering the acquisition means information in a case where a predetermined sample acquisition operation is performed, and deliver the operation check information; and
determine whether or not the image or the video acquired by the input-output interface from the user terminal is normal, wherein
during the sample acquisition operation,
in a case where it is determined that the sample acquisition operation is normal, the at least one processor is further configured to release the stop of the delivery of the acquisition means information and resume the delivery of the acquisition means information,
in a case where it is determined that the sample acquisition operation is abnormal, the at least one processor is further configured to deliver the operation check information again,
the at least one processor is further configured to measure a time having passed from a start of the delivery of the operation check information until acquisition of the image or the video, and adjust a delivery speed of the acquisition means information according to a length of the time,
in a case where the at least one processor receives an operation to stop the delivery of the operation check information from the user terminal, or in a case where the at least one processor cannot receive the image or the video within a predetermined time, the delivery speed of the operation check information is reduced, and
in a case where the at least one processor further receives the operation to stop the delivery of the operation check information, or in a case where the at least one processor cannot receive the image or the video, the delivery speed of the operation check information is further reduced.

11. The sample acquisition information management system according to claim 10,
wherein the terminal is a portable terminal of the subject.

12. The sample acquisition information management system according to claim 10,
wherein the terminal comprises:
a display configured to display the acquisition means information and the operation check information; and
a camera configured to take the image and the video of the sample acquisition operation.

13. A sample acquisition information management method using a sample acquisition information management system including a server configured to be connectable to a terminal through a network, the sample acquisition information management method comprising:

a step of delivering, from the server, acquisition means information according to a request from a user terminal of a subject to cause a display of the user terminal to display the acquisition means information;

a step of stopping delivery of the acquisition means information in a case where a predetermined sample acquisition operation is performed, and delivering, from the server, operation check information to cause the display of the user terminal to display the operation check information;

a step of acquiring, from the user terminal, at least one of an image or a video of a sample acquisition operation of the subject using an examination kit;

a step of determining by the server, whether or not the image or the video corresponds to a normal sample acquisition operation; and a step of releasing, by the server, the stop of the delivery of the acquisition means information to the user terminal and resuming the delivery of the acquisition means information in a case where it is determined that the sample acquisition operation is normal, and delivering, from the server, the operation check information to the user terminal again in a case where it is determined that the sample acquisition operation is abnormal, wherein the method further comprises:

measuring a time having passed from a start of the delivery of the operation check information until acquisition of the image or the video; and adjusting a delivery speed of the acquisition means information according to a length of the measured time by the server, in a case where the server receives an operation to stop the delivery of the operation check information from the user terminal, or in a case where the server cannot receive the image or the video within a predetermined time, reducing the delivery speed of the operation check information, in a case where the server further receives the operation to stop the delivery of the operation check information, or in a case where the server cannot receive the image or the video, further reducing the delivery speed of the operation check information.

* * * * *